United States Patent [19]

Miyano et al.

[11] Patent Number: 4,888,356
[45] Date of Patent: * Dec. 19, 1989

[54] USE OF SUBSTITUTED DIHYDROBENZOPYRANS FOR ALLERGY AND INFLAMMATION

[75] Inventors: Masateru Miyano, Northbrook; Robert L. Shone, Palatine, both of Ill.; Daniel D. Sohn, Uppsala, Sweden

[73] Assignee: G. D. Searle and Company, Chicago, Ill.

[*] Notice: The portion of the term of this patent subsequent to Oct. 18, 2005 has been disclaimed.

[21] Appl. No.: 206,624

[22] Filed: Jun. 14, 1988

Related U.S. Application Data

[60] Continuation of Ser. No. 681,038, Dec. 12, 1984, Pat. No. 4,778,903, which is a division of Ser. No. 560,355, Dec. 12, 1983, abandoned, which is a continuation-in-part of Ser. No. 520,973, Aug. 8, 1983, abandoned.

[51] Int. Cl.$^4$ .................... A61K 31/35; A61K 31/40; A61K 31/445
[52] U.S. Cl. .................................... 514/456; 514/422; 514/320
[58] Field of Search ................. 549/405, 407; 548/525; 546/196; 514/456, 422, 320

[56] References Cited

U.S. PATENT DOCUMENTS

| | | | |
|---|---|---|---|
| 3,953,604 | 4/1976 | Warren et al. | 424/283 |
| 4,001,280 | 1/1977 | Umle et al. | 549/402 |
| 4,006,245 | 2/1977 | Augustin et al. | 424/283 |
| 4,156,726 | 5/1979 | Brown et al. | 424/258 |
| 4,213,903 | 7/1980 | Bantick et al. | 548/250 |
| 4,238,495 | 12/1980 | Warren et al. | 424/269 |
| 4,281,008 | 7/1981 | Chamberlain et al. | 424/269 |
| 4,328,230 | 5/1982 | Brown et al. | 424/256 |

FOREIGN PATENT DOCUMENTS

| | | |
|---|---|---|
| 79637 | 5/1983 | European Pat. Off. |
| 1291864 | 10/1972 | United Kingdom |
| 1291865 | 10/1972 | United Kingdom |

*Primary Examiner*—Nicky Chan
*Attorney, Agent, or Firm*—Mary Jo Kanady; Paul D. Matukaitis

[57] ABSTRACT

The invention relates to compounds of the formula:

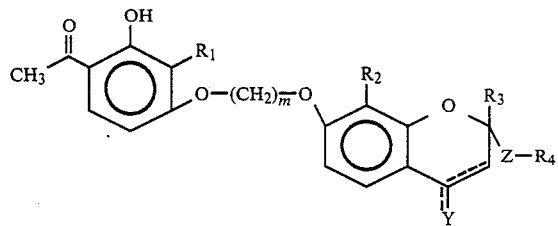

which are useful as leukotriene D$_4$ (LTD$_4$) inhibitors and therefore useful in the treatment of allergies and inflammatory conditions.

24 Claims, No Drawings

USE OF SUBSTITUTED DIHYDROBENZOPYRANS FOR ALLERGY AND INFLAMMATION

This is a continuation of application Ser. No. 0/681,038 filed Dec. 12, 1984, l now U.S. Pat. No. 4,778,903, which is a divisional application of prior co-pending application Ser. No. 560,355, filed Dec. 12, 1983, now abandoned, which in turn is a continuation-in-part of application Ser. No. 520,973 filed Aug. 8, 1983, now abandoned.

BACKGROUND OF THE INVENTION (a) Field of the Invention

This application is a continuation-in-part of application Ser. No. 0/520,973 filed Aug. 8, 1983. This invention in its broadest aspect, relates to metabolic inhibitors. In particular the invention relates to novel compounds of Formula I which are inhibitors of leukotriene $D_4$ ($LTD_4$) and therefore useful to prevent or alleviate the symptoms or conditions associated with $LTD_4$ such as allergic reactions and inflammatory conditions.

$LTD_4$ is a product of the 5-lipoxygenase pathway and is the major active constituent of slow reacting substance of anaphylaxis (SRS-A) in humans and guinea pigs, Lewis et al., Nature USA, 293: 103-108, (1981). It is a potent bronchoconstrictor that is released during allergic reactions. Because antihistamines are ineffective in the management of asthma it is believed that SRS-A mediates bronchoconstriction resulting from an allergic attack. SRS-A is also a potent inducer of vascular permiability, and it also may be involved in other inflammatory conditions such as rheumatoid arthritis.

(b) Information Disclosure

Appleton et al., J. Med. Chem. 20, 371-379 (1977) discloses a series of chromone-2-carboxylic acids which are antagonists of SRS-A. Specifically sodium 7-[3-(4-acetyl-3-hydroxy-2-propylphenoxy)-2-hydroxypropoxy]-4-oxo-8-propyl-4H-1-benzopyran-2-carboxylate (FPL 55712), appears to be the first reported specific antagonist of SRS-A and $LTD_4$.

SUMMARY OF THE INVENTION

The invention relates to compounds of the formula:

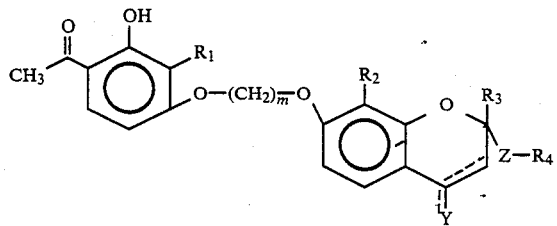

wherein Z is:
(a) —$(CH_2)_n$—; or
(b) —$(CH_2)_p$—CH=CH—$(CH_2)_q$—; $(CH_2)_r$,
(c) —$(CH_2)_s$—CH—CH—$(CH_2)_t$;
(d) —CO—$(CH_2)_w$—; or
(e) —CHOH—$(CH_2)_v$—;

wherein l is an integer of from zero to 2 inclusive;
wherein m is an integer of from 2 to 6 inclusive;
wherein n is an integer of from 1 to 3 inclusive;
wherein p is an integer of from zero to 4 inclusive;
wherein q is an integer of from zero to 4 inclusive;
wherein p+q is equal to or less than 6;
wherein r is an integer of from 1 to 5 inclusive;
wherein s is an integer of from zero to 4 inclusive;
wherein t is an integer of from 0 to 4 inclusive;
wherein w is an integer of from 1 to 6 inclusive;
wherein v is an integer of from 1 to 6 inclusive;
wherein Y is:
(a) —H;
(b) =$H_2$; —H,
(c) —OH; or
(d) =O;
with the proviso that the double bond at the 3-4 position may be present only when Y is H;
wherein $R_1$, $R_2$, $R_5$ and $R_6$ are:
(a) alkyl of 1 to 6 carbon atoms, inclusive, each being the same or different;
wherein $R_3$ is:
(a) alkyl of 1 to 6 carbon atoms, inclusive;
(b) —COOH; or
(c) —$(CH_2)_l COOR_5$;
with the proviso that $R_3$ is hydrogen when Y is not =O;
wherein $R_4$ is:
(a) hydrogen;
(b) —$CO_2H$;
(c) —$CO_2R_6$;
(d) —$CONR_7R_8$; or
(e) —OH
wherein $R_7$ and $R_8$ are:
(a) hydrogen
(b) alkyl of 1 to 6 carbon atoms, inclusive: $R_7$ and $R_8$ each being the same or different; or
(c) taken together to form a 5 or 6 member ring optionally substituted by carboxylic acid or methyl ester thereof with the balance of the members being carbon;
or the pharmacologically acceptable addition salts thereof.

Examples of alkyl or 1 to 6 carbon atoms inclusive are methyl, ethyl, propyl, butyl, pentyl, hexyl, and the isomeric forms thereof.

Salts of the acid forms of these compounds can be prepared by neutralization with the appropriate amount of an inorganic or organic base such as sodium hydroxide, potassium hydroxide, calcium hydroxide, magnesium hydroxide, ammonia, trialkylamine, dialkylamine, monoalkylamine, dibasic amino acids, sodium acetate, potassium benzoate, triethanolamine and like bases.

$LTD_4$ causes bronchoconstriction when administered to humans and guinea pigs. The bronchoconstriction has 2 components: (a) a direct stimulation of respiratory smooth muscle by $LTD_4$ and (b) an indirect component through release of thromboxane A2 which in turn causes contraction of respiratory smooth muscle. Compounds of the invention antagonize the direct component. The compounds are tested in vivo as follows.

Adult male fasted Hartly guinea pigs weighing 300-350 g are pretreated with pyrilamine and indomethacin to block the bronchoconstricture effects of endogenous histamine and the synthesis of thromboxane A2 respectively. Compounds of the invention are administered IV or IG at appropriate times prior to the IV administration of 2000 units of $LTD_4$. Intratracheal pressure is monitored prior to and subsequent to $LTD_4$ in animals anesthetized with pentobarbital and attached to a rodent respirator. Compounds which antagonize the direct component of $LTD_4$ action on respiratory smooth muscle inhibit intratracheal insufflation pressure increases (P or =0.05) caused by LTD$_4$. FPL 55712 is used as a control.

The compounds can be administered in a number of dosage forms. A preferred method of delivery would be oral or in such a manner so as to localize the action of the inhibitor. For example, for asthma, the compounds could be inhaled using an aerosol or other appropriate spray. In an inflammatory condition such as rheumatoid arthritis the compounds could be injected directly into the affected joint. The compounds could also be administered in oral unit dosage forms such as tablets, capsules, pills, powders or granules. They also may be administered rectally or vaginally in such forms as suppositories. They may be introduced in the forms of eyedrops, intraperitoneally, subcutaneously, or intramuscularly using forms known to the pharmaceutical art. For the treatment of inflammatory allergic skin conditions, the compounds of the present invention may also be administered topically in the form of ointments, creams, gels or the like. Regardless of the route of administration selected, the compounds are formulated into pharmaceutically acceptable dosage forms by conventional methods known to the pharmaceutical art.

An effective but non-toxic quantity of the compound is employed in treatment. The dosage regimen for inhibition of LTD$_4$ by the compounds of this invention is selected in accordance with a variety of factors including the type, age, weight, sex, and medical condition of the mammal, the particular disease and its severity, the route of administration and the particular compound employed. An ordinarily skilled physician or veterinarian will readily determine and prescribe the effective amount of the compound to prevent or arrest the progress of the condition. In so proceeding, the physician or veterinarian could employ relatively low dosages at first, subsequently increasing the dose until a maximum response is obtained.

The compounds of this invention are prepared by the general methods illustrated in Charts A to E. The various compounds and intermediates can be readily modified by methods known to those skilled in the art. For example, esters can be hydrolyzed to corresponding carboxylic acids (and their respective addition salts), converted to corresponding amides by appropriate reactions with amines, and reduced to alcohols by such reagents as Lithium borohydride. Such products and intermediates can, of course, be similarly interconverted.

As illustrated in Chart A, 2-hydroxyacetophenones of Formula XI react readily with ketones of Formula XII to afford fused ring compounds of Formula XIII. Ketones, Formula XII, include ketoesters in which Z is alkylene or alkenylene and R$_4$ is alkoxycarbonyl. An example of such a ketoester is ethyl levulinate. Preferred condensation and cyclization conditions include heating Formulas XI and XII at reflux in toluene, in the presence of a base such as pyrrolidine, with provisions for the removal of water with an apparatus such as a Dean-Stark trap. Intermediates of Formula XIII thus formed may be used in reactions of Chart B without further modification or they may be converted to related intermediates, Formula XIV, by methods known to those skilled in the art. For example, hydrogenation over palladium on carbon will reduce the keto function of Formula XIII to the corresponding dihydrobenzopyran, Formula XIV (Y=H$_2$). Partial hydrogenation would afford corresponding hydroxyl compounds (Y=H, OH).

As illustrated in Chart B, compounds of Formula XIV may be alkylated under basic conditions to form compounds of Formula XXI. Preferred reagents include dihaloalkanes, such as 1,3-dibromopropane and the like. Preferred conditions include reaction in dry dimethylformamide in the presence of anhydrous potassium carbonate. Intermediates XXI are typically purified by column chromatography on silica gel. Reaction of these intermediates with 2-hydroxyacetophenones of Formula XXII afford title compounds of this invention, Formula XXIII. Preferred conditions include reaction in dry dimethylformamide in the presence of anhydrous potassium carbonate. Alternatively, the reaction may be run under phase transfer conditions.

Chart C illustrates preparation of compounds XXIII using a variation of the method of Chart B. 2-Hydroxyacetophenones of Formula XXII react with dihaloalkanes as described above (See Chart B) to form intermediates of Formula XXXI. By the same general procedure employed in converting Formula XIV to Formula XXI, compounds XXXI and XIV react to form the title compounds of this invention, Formula XXIII.

Chart D illustrates another route for preparing some of the compounds of this invention. Benzopyrones of Formula XLI, previously described in the literature, can be reduced by catalytic hydrogenation to compounds of Formula XLII, where Y may range from =O to (H, OH) to H$_2$, which can be further modified by methods known to those skilled in the art. For example, the hydroxyl compounds (Y=H, OH) can be dehydrated to form benzopyrans of Formula XLIII. Methods include conversion to the mesylate derivatives, followed by elimination under basic conditions to form Formula XLIII. As another example, esters (R$_4$=COO(alkyl)) can be reduced with active metal hydrides, such as Lithium borohydride, to give corresponding alcohols of Formula XLIV.

Chart E also illustrates another approach to preparing some of the compounds of this invention. Compounds of Formula LI (in which R$_{11}$ may be a protecting group to be removed for later elaboration or may consist of the ultimate aromatic side chain already prepared as generally described above) are first treated with strong base in an unreactive solvent. Preferred reagents include n-butyl lithium in tetrahydrofuran. Alkylation affords compounds of Formula LII. Examples of alkylating reagents include simple alkyl halides or substituted alkyl halides, such as iodoalkylcarboxylic ester, beta-unsaturated carboxylic esters (which undergo conjugate additions), and many other reagents known to those skilled in the art. Further conversions of compounds LII can produce other derivatives, such as free carboxylic acids, Formula LIII, which can be formed by hydrolysis of compounds LII. Acylation of compounds LI under similar conditions afford compounds of Formula LIV. Acylating reagents include acyl halides or other activated acyl derivatives. Preferred reagents include substituted N-alkanoylimidazole derivatives. Compounds of Formula LIV can also be converted to other derivatives. For example, basic hydrolysis leads to decarboxylated compounds of Formula LV.

The invention will appear more fully from the Examples which follow. These Examples are given by way of illustration only and are not to be construed as limiting the invention either in spirit or in scope, as many modifications both in materials and methods will be apparent from this disclosure to those skilled in the art. In these examples, temperatures are given in degrees celcius (°C.) and quantities of materials in grams and milliliters unless otherwise noted.

DESCRIPTION OF THE PREFERRED EMBODIMENTS

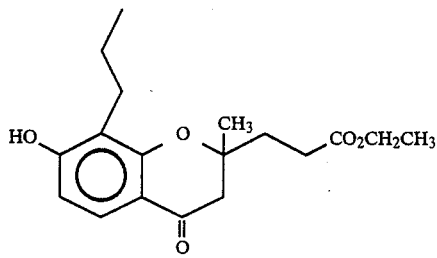

EXAMPLE 1 ethyl 3-(3,4-dihydro-7-hydroxy-2-methyl-4-oxo-8-propyl-2H-1-benzopyran-2-yl)propanoate A solution of 58.0 g (0.299 mole) of 2,4-dihydroxy-3-propylacetophenone and 29.5 ml (0.36 mole) of pyrrolidine in 250 ml of toluene was heated to reflux for three hours under a Dean-Stark trap. After cooling the mixture, 68.2 ml (0.48 mole) of ethyl levulinate was added and the mixture was refluxed for two hours. An additional 10 ml (0.12 mole) of pyrrolidine was added and the mixture was refluxed overnight under a Dean-Stark trap.

The reaction mixture was diluted with ethyl acetate and washed successively with water, 2M hydrochloric acid, water and brine. It was then dried over MgSO$_4$, filtered, and evaporated to dryness. The residue was chromatographed on silica gel using 30% ethyl acetate/hexane as eluent to give 35.5 g of the title ester, mp. 92°–94° C. Structure assignment was confirmed by nmr and infrared spectra.

IR(CHCl$_3$): 1665, 1730 cm$^{-1}$.

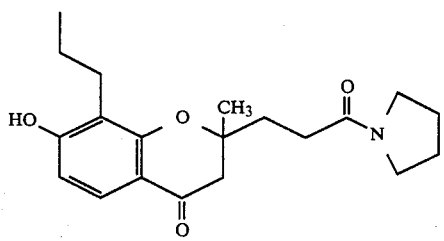

EXAMPLE 2

1-[3-(3,4-dihydro-7-hydroxy-2-methyl-4-oxo-8-propyl-2H-1-benzopyran-2-yl)-1-oxopropyl]pyrrolidine Other chromatographic fractions of Example 1 afforded 30 g of the title amide, m.p. 182°–184°. Structure assignment was confirmed by nmr and infrared spectra and by elemental analysis.

IR(KBr): 1615, 1675 cm$^{-1}$.

Analysis. Calcd. for C$_{20}$H$_{27}$NO$_4$: C, 69.54; H, 7.88; N, 4.05. Found: C, 69.22; H, 7.93; N, 3.97.

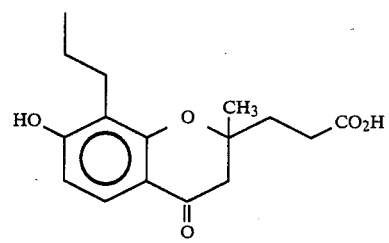

EXAMPLE 3

3-(3,4-dihydro-7-hydroxy-2-methyl-4-oxo-8-propyl-2H-1-benzopyran-2-yl)propanoic acid To a mixture of 20.0 g (103 mmole) of 2,4-dihydroxy-3-propylacetophenone and 15.5 g (134 mmole) of methyl levulinate in 100 ml of dry toluene was added by syringe 21.5 ml (ca. 260 mmole) of pyrrolidine. After stirring for one hour the solution was heated on a steam bath for four hours and allowed to cool. The toluene solution was washed with water and 2N NaOH. The basic solution was acidified and extracted with diethyl ether, which in turn was extracted with saturated sodium bicarbonate. The basic aqueous extract was neutralized with dilute hydrochloric acid and again extracted with diethyl ether. After drying, the solution was concentrated at reduced pressure to an oil which crystallized to the title compound, m.p. 152°–153°.

Analysis calcd. for C$_{16}$H$_{20}$O$_5$: C, 65.74; H, 6.90. Found: C. 65.24; H, 6.86.

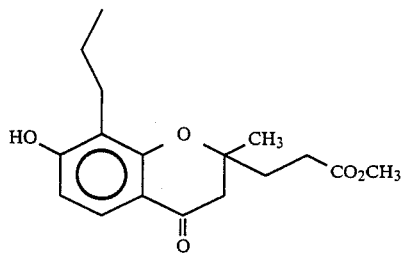

EXAMPLE 4 methyl 3-(3,4-dihydro-7-hydroxy-2-methyl-4-oxo-8-propyl-2H-1-benzopyran-2-yl)propanoate A mixture of the title compound of Example 3 (4.3 g, 14.7 mmole), 6 ml of trimethylorthoformate, and 1.4 ml of sulfuric acid was stirred at room temperature for two hours. The reaction mixture was poured onto stirred ice/water and extracted with ethyl acetate. The organic phase was washed with water, dried over magnesium sulfate, and concentrated to an oil. The oil was purified by chromatography on silica gel, giving 3.7 g of the title compound as a crystalline solid, m.p. 101.5°–102.5°. Structure assignment was consistent with nmr and infrared spectra.

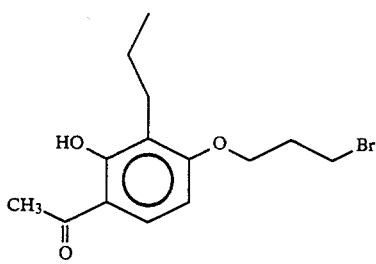

EXAMPLE 5

4-(3-bromopropoxy)-2-hydroxy-3-propylacetophenone

To a mixture of 50.0 g (257 mmole) of 2,4-dihydroxy-3-propylacetophenone, 87.4 g (257 mmole) of tetrabutylammonium hydrogen sulfate, and 52.2 ml (ca. 514 mmole) of dibromopropane in 250 ml of dichloromethane was added 225 ml (450 mmole) of 2N NaOH. The mixture was then heated at reflux for about 30 min. and allowed to cool. After concentrating the reaction mixture under vacuum, the residue was triturated with diethyl ether, and the ether solution was filtered and concentrated to dryness. After purification by column chromatography on silica gel, the title compound was isolated and used in subsequent reactions without further characterization.

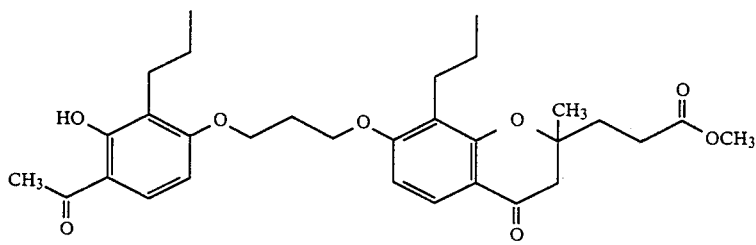

EXAMPLE 6 methyl 3-[7-[3-(4-acetyl-3-hydroxy-2-propylphenoxy)propoxy]-3,4-dihydro-2-methyl-4-oxo-8-propyl-2H-1-benzopyran-2-yl]propanoate A mixture of 1.9 g (6.2 mmole) of the ester product of Example 4, 2.2 g (6.8 mmole) of the title product of Example 5, and 1.8 g (13 mmole) of anhydrous potassium carbonate in 30 ml of dry dimethylformamide was stirred for 16 hours at room temperature. The inorganic salts were removed by filtration and the dimethylformamide was evaporated in vacuo. The residue was dissolved in ethyl acetate and additional inorganic salts were filtered. The filtrate was evaporated and the residue was chromatographed on silica gel using 7% ethyl acetate/toluene as eluent to afford 2.5 g of the title compound, mp. 73°-74.5°. Structure assignment was confirmed by nmr and infrared spectra and by elemental analysis.

nmr (CDCl$_3$): δ(ppm) 0.89 (t, J=7.5 Hz, 6H, propyl CH$_3$'s); 1.24 (t, J=7 Hz, 3H, ester CH$_3$); 1.35 (s, 3H, 2-methyl protons); 2.55 (s, 3H, acetyl CH$_3$); 4.22 (t, J=6 Hz, 4H, OCH$_2$'s); 6.42, 6.53, 7.54, 7.71 (sets of d's, aromatic).

IR(CHCl$_3$): 1625, 1675, 1730 cm$^{-1}$.

Analysis. Calcd. for C$_{31}$H$_{40}$O$_8$: C, 68.87; H, 7.46. Found: C, 69.12; H, 7.44.

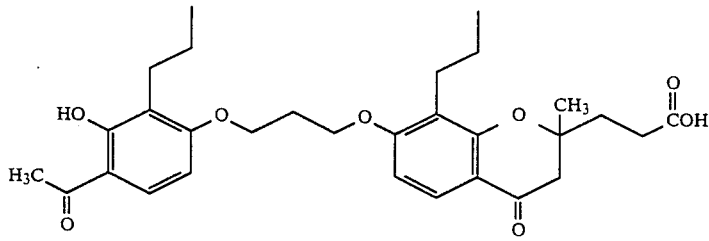

EXAMPLE 7

3-[7-[3-(4-acetyl-3-hydroxy-2-propylphenoxy)propoxy]-3,4-dihydro-2-methyl-4-oxo-8-propyl-2H-1-benzopyran-2-yl]propanoic acid A solution of 0.5 g (19.5 mmole) of lithium hydroxide in 10 ml of water was added to a solution of 2.2 g (3.9 mmole) of the title compound of Example 6 in 25 ml of tetrahydrofuran and 20 ml of methanol. After the reaction mixture was stirred for 3 hours at room temperature, the solvent was evaporated and water was added to the residue. After extracting with a small amount of diethyl ether, the aqueous layer was acidified with dilute hydrochloric acid and allowed to stand in the cold overnight. The solid was filtered, washed with water and recrystallized from ethyl acetate/hexane to yield 1.83 g of the title compound, mp. 80°-83°. Structure assignment was confirmed by nmr and infrared spectra and by elemental analysis.

nmr (CDCl$_3$): loss of ester CH$_3$ (compare Example 6).
IR(KBr): 1625, 1675, 1710, 1730 cm$^{-1}$.
Analysis. Calcd. for C$_{31}$H$_{38}$O$_8$.H$_2$O: C, 66.16; H, 7.40. Found: C, 66.15; H, 7.44.

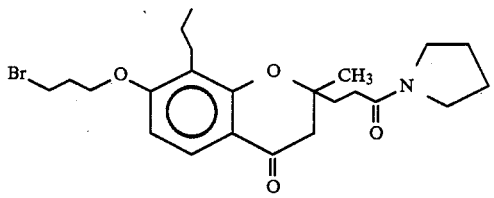

EXAMPLE 8

1-[3-(7-(3-bromoproxy)-3,4-dihydro-2-methyl-4-oxo-8-propyl-2H-1-benzopyran-2-yl)-1-oxopropyl]pyrrolidine The title compound, mp 103°–104°, was prepared by the method of Example 6 using the amide pyrrolidone product of Example 2 and 1,3-dibromopropane as starting materials. Structure assignment was confirmed by nmr and infrared spectra and by elemental analysis.

IR(CHCl$_3$): 1625, 1675 cm$^{-1}$.

Analysis. Calcd. for C$_{23}$H$_{32}$BrNO$_4$: C, 59.23; H, 6.92; N, 3.00. Found: C, 59.44; H, 6.96; N, 2.84.

EXAMPLE 20 methyl 3-(3,4-dihydro-7-hydroxy-2-methyl-8-propyl-2H-1-benzopyran-2-yl)propanoate A solution of 4.1 g (13.4 mmole) of ester product of Example 4 in 100 ml of acetic acid and 50 ml of methanol was hydrogenated for 21 hours at 4 psi and room temperature using palladium on carbon as catalyst. The catalyst was filtered and the filtrate was evaporated to dryness. Chromatography of the residue on silica gel using 20% ethyl acetate/hexane as eluent gave 1.8 g of the title compound as an oil. Structure assignment was confirmed by nmr and infrared spectra.

nmr (CKCl$_3$): δ(ppm) 0.94 (t, J=7 Hz, 3H, propyl CH$_3$); 1.23 (s, 3H, 2-methyl protons); 3.67 (s, 3H, ester CH$_3$); 6.28 (d, J=8 Hz, 1H, aromatic); 6.71 (d, J=8 Hz, 1H, aromatic).

IR(CHCl$_3$): 1730 cm$^{-1}$.

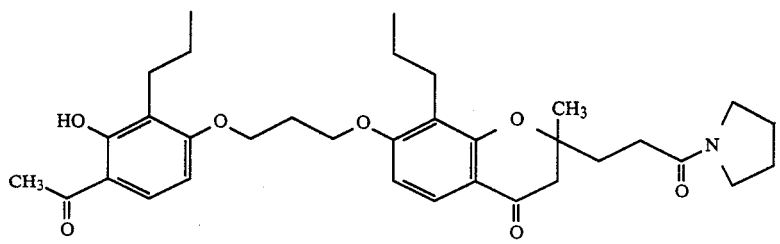

EXAMPLE 9

1-[3-[7-[3-(4-acetyl-3-hydroxy-2-propylphenoxy)-propoxy]-3,4-dihydro-2-methyl-4-oxo-8-propyl-2H-1-benzopyran-2-yl]-1-oxopropyl]pyrrolidine The title compound, mp 93°–94.5°, was prepared by the method of Example 6 using the title compound of Example 8 and 2,4-dihydroxy-3-propylacetophenone as starting materials. Structure assignment was confirmed by nmr and infrared spectra and by elemental analysis.

IR(CHCl$_3$): 1625, 1675 cm$^{-1}$.

Analysis. Calcd. for C$_{34}$H$_{45}$NO$_7$: C, 70.44; H, 7.82; N, 2.42. Found: C, 70.32; H, 7.78; N, 2.35.

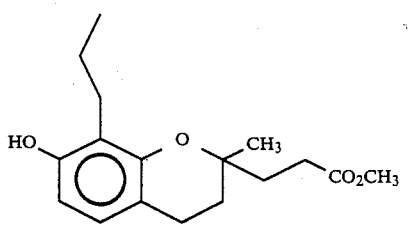

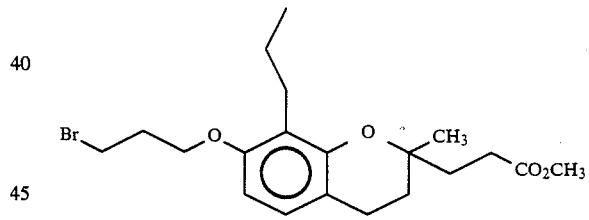

EXAMPLE 11 methyl 3-[7-(3-bromopropoxy)3,4-dihydro-2-methyl-8-propyl-2H-1-benzopyran-2-yl]propanoate To a solution of 1.7 g (5.51 mmole) of the title compound from Example 10, 1.1 ml (11 mmoles) of 1,3-dibromopropane and 1.9 g (11 mmole) of tetrabutylammonium hydrogen sulfate in 12 ml of methylene chloride was added 5.5 ml of 2M sodium hydroxide solution. The reaction mixture was heated to reflux for 15 minutes and cooled. The organic layer was separated, washed with brine, dried over sodium sulfate, filtered, and concentrated to dryness. Chromatography of the residue on silica gel using 10% ethyl acetate/hexane as eluent gave 1.8 g of the title compound as an oil. Structure assignment was confirmed by nmr and infrared spectra.

nmr (CDCl$_3$): addition of CH$_2$Br signal at δ(ppm) 4.02 (t, J=6 Hz) (compare Example 10).

IR(CHCl$_3$): 1735 cm$^{-1}$.

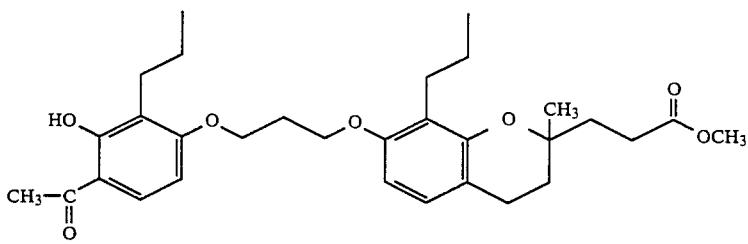

EXAMPLE 12 methyl 3-[7-[3-(4-acetyl-3-hydroxy-2-propylphenoxy)propoxy]-3,4-dihydro-2-methyl-8-propyl-2H-1-benzopyran-2-yl]propanoate The title compound mp. 53°-55°, was prepared by the method of Example 6 using the product of Example 11 and 2,4-dihydroxy-3-propylacetophenone as starting materials. Structure assignment was confirmed by nmr and infrared spectra and by elemental analysis.

IR(CHCl$_3$): 1625, 1730 cm$^{-1}$.

Analysis. Calcd. for $C_{31}H_{42}O_7$: C, 70.70; H, 8.04. Found: C, 70.59; H, 8.10.

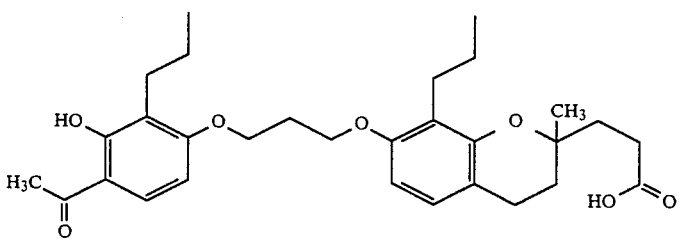

EXAMPLE 13

3-[7-[3-(4-acetyl-3-hydroxy-2-propylphenoxy)propoxy]-3,4-dihydro-2-methyl-8-propyl-2H-1-benzopyran-2-yl]propanoic acid The title compound was prepared by the method of Example 7 using the product of Example 12 as starting material, except that the acidified aqueous layer was extracted with ethyl acetate. The organic layer was then washed with water and brine, dried over MgSO$_4$, filtered, and evaporated to dryness to afford the title compound as an oil. Structure assignment was confirmed by nmr and infrared spectra and by elemental analysis.

IR(KBr): 1620, 1705, 1735 cm$^{-1}$.

Analysis. Calcd. for $C_{30}H_{40}O_7$: C, 70.29; H, 7.87. Found: C, 69.93; H, 7.77.

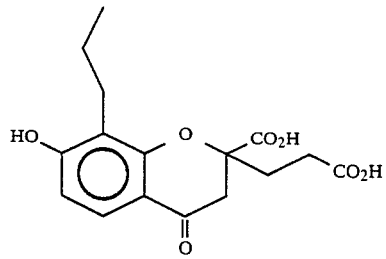

EXAMPLE 14

3-(2-carboxy-3,4-dihydro-7-hydroxy-4-oxo-8-propyl-2H-1-benzopyran-2-yl)propanoic acid The title compound was prepared by the method of Example 1 using α-ketoglutaric acid as starting material. The crude product was used without further purification. α-ketoglutaric acid can be replaced with homolegues, for instance, 4-ketopinslic acid to produce homologous of the title compound.

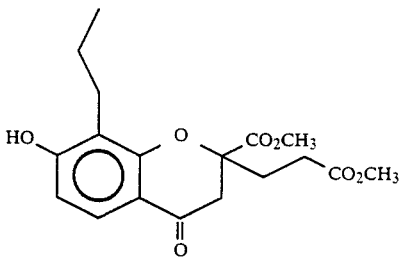

EXAMPLE 15 methyl 3-(3,4-dihydro-7-hydroxy-2-methoxy carbonyl-4-oxo-8-propyl-2H-1-benzopyran-2-yl) propanoate To a solution of 13 g of the crude product of Example 14 in 250 ml of methanol and 25 ml of trimethylorothoformate was added 5 ml of sulfuric acid. The reaction mixture was stirred for 12 hours at room temperature, poured onto an ice/water mixture, and extracted with ethyl acetate. The organic layer was washed successively with water, 5% sodium bicarbonate solution, water and brine, dried over MgSO₄, filtered, and evaporated to dryness. Chromatography of the residue on silica gel using 13% ethyl acetate/hexane as eluent gave 6.1 g of the title compound. Structure assignment was confirmed by nmr and infrared spectra.

nmr (CDCl₃): δ(ppm) 0.99 (t, J=6 Hz, 3H, propyl CH₃); 3.64, 3.71 (pair s, 6H, ester CH₃'s); 6.45, 7.56 (pair d's, aromatic).

IR(CHCl₃): 1685, 1740 cm⁻¹.

washed with water and brine, dried over MgSO₄, filtered, and evaporated to dryness to give the title compound. Structure assignment was confirmed by nmr and infrared spectra and by elemental analysis.

nmr (CDCl₃): loss of ester CH₃'s (compare Example 16).

IR(KBr): 1620, 1680, 1710–1740 cm⁻¹.

Analysis. Calcd. for C₃₀H₃₆O₁₀.H₂O: C, 62.71; H, 6.67. Found: C, 62.85; H, 6.64.

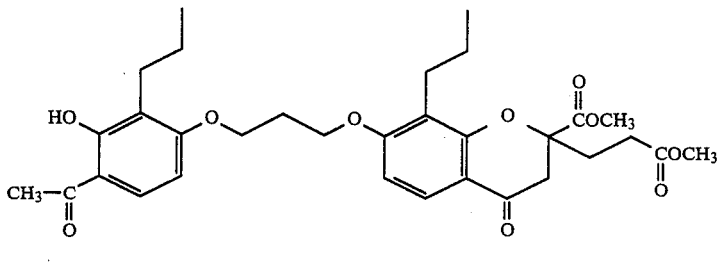

EXAMPLE 16 methyl 3-[7-(3-(4-acetyl-3-hydroxy-2-propyl phenoxy)propoxy]-3,4-dihydro-2-methoxy carbonyl-4-oxo-8-propyl-2H-1-benzopyran-2-yl)propanoate The title compound was prepared by the method of Example 2 using the product of Example 11 as starting material. Structure assignment was confirmed by nmr and infrared spectra and by elemental analysis substituting appropriate compounds homologs where 1 is 1 or 2 may be made.

nmr (CDCl₃): δ(ppm) 0.88, 0.93 (pair t, 6H, propyl CH₃'s); 2.56, (s, 3H, acetyl CH₃); 3.61, 3.68 (pair s, 6H, ester CH₃'s) 4.21 (t, J=7 Hz, 4H, OCH₂'s); 6.39, 6.55, 7.53, 7.66 (sets of d's, aromatic).

IR(CHCl₃): 1630, 1685, 1740 cm⁻¹.

Analysis. Calcd. for C₃₂H₄₀O₁₀: C, 65.74; H, 6.90. Found: C, 65.89; H, 6.87.

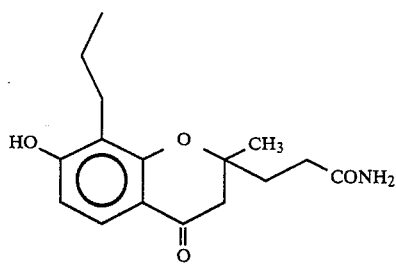

EXAMPLE 18

3-(3,4-dihydro-7-hydroxy-2-methyl-4-oxo-8-propyl-2H-1-benzopyran-2-yl)propanamide To a solution of the title product of Example 3, (1.0 g, 3.4 mmole) in 50 ml of dry tetrahydrofuran cooled to 0° was added 2.1 g (10.2 mmole) of phosphorus pentachloride. After the mixture was stirred for 30 minutes, approximately 2 ml of liquid ammonia was added, and the solution was warmed to room temperature and stirred

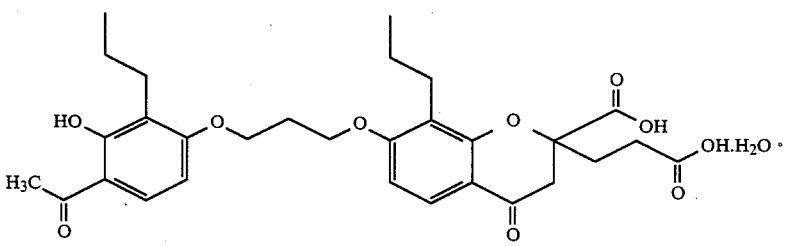

EXAMPLE 17

3-[7-[3-(4-acetyl-3-hydroxy-2-propylphenoxy) propoxy]-2-carboxy-3,4-dihydro-4-oxo-8-propyl-2H-1-benzopyran-2-yl]propanoic acid The title compound, mp. 76°–79°, was prepared by the method of Example 7 using the product of Example 16 as starting material, except that ten equivalents of lithium hydroxide were used. The acidified aqueous layer was extracted into ethyl acetate, which was then for an additional 30 minutes. The solvent was evaporated and the residue was dissolved in ethyl acetate. The organic layer was washed successively with saturated sodium bicarbonate solution, water, and brine, dried over MgSO₄, filtered, and concentrated to dryness. The crude product, mp. 108°–115°, was not purified further. Structure assignment was supported by nmr and infrared spectra.

IR(KBr): 1680 cm⁻¹.

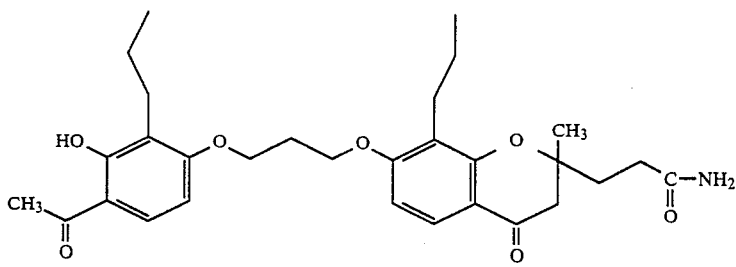

EXAMPLE 19

3-[7-[3-(4-acetyl-3-hydroxy-2-propylphenoxy)propoxy]-3,4-dihydro-2-methyl-4-oxo-8-propyl-2H-1-benzopyran-2-yl]propanamide The title compound, mp 77°–79°, was prepared by the method of Example 6 using the amide product of Example 18 as starting material, except that after stirring at room temperature for 16 hours the reaction mixture was further heated at 50° for three hours. Structure assignment was confirmed by nmr and infrared spectra and by elemental analysis.

IR(KBr): 1630, 1675 cm$^{-1}$.

Analysis. Calcd. for $C_{30}H_{39}O_7$: C, 68.55; H, 7.48; N, 2.66. Found: C, 68.62; H, 7.81; N, 2.49.

EXAMPLE 20

3-(3,4-dihydro-7-hydroxy-N,N,2-trimethyl-4-oxo-8-propyl-2H-1-benzopyran-2-yl)propanamide To a solution of the title product of Example 3, (1.0 g, 3.4 mmole) in 40 ml of dry dimethylformamide cooled to −20° was added 0.37 ml (3.4 mmole) of N-methylmorpholine, followed by a solution of 0.45 ml (3.4 mmole) of isobutylchloroformate in 3 ml of dimethylformamide. The reaction miture was stirred at −30° for about twenty minutes, after which gaseous dimethylamine was bubbled through for two minutes. After twenty minutes' stirring, the mixture was allowed to warm to room temperature and stirred an additional 30 minutes. The solvent was evaporated and the residue was dissolved in ethyl acetate, which was washed successively with saturated sodium bicarbonate solution, water, and brine, then dried over MgSO$_4$. Filtration and removal of the solvent gave 0.84 g of the title compound, mp. 108°–110°. Structure assignment was confirmed by nmr and infrared spectra.

nmr (CDCl$_3$): δ(ppm) 0.97(t, J=7 Hz, 3H, propyl CH$_3$); 1.39, (s, 3H, 2-methyl protons); 2.89, 3.09 (pair s, 6H, N(CH$_3$)$_2$); 6.55 7.52 (sets of d's, aromatic).

IR(KBr): 1625, 1985 cm$^{-1}$.

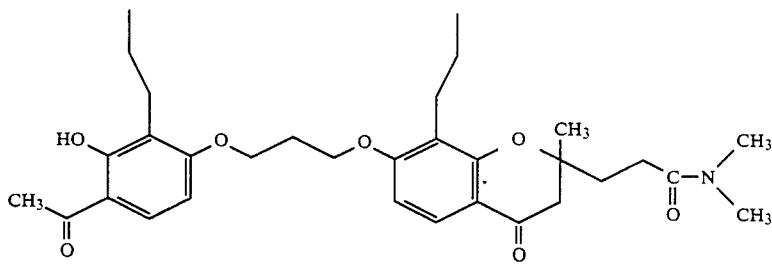

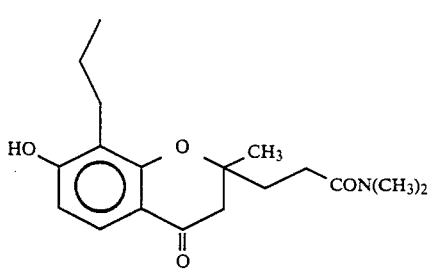

EXAMPLE 21

3-[7-[3-(4-acetyl-3-hydroxy-2-propylphenoxy)propoxy]-3,4-dihydro-N,N,2-trimethyl-4-oxo-8-propyl-2H-1-benzopyran-2-yl]propanamide The title compound, mp. 126°–128°, was prepared by the method of Example 6 using the amide product of Example 20 as starting material. Structure assignment was confirmed by nmr and infrared spectra and by elemental analysis.

nmr (CDCl$_3$): additional signals for aryloxypropoxy protons (compare Example 20).

IR(KBr): 1635, 1685 cm$^{-1}$.

Analysis: Calcd. for $C_{32}H_{43}NO_7$: C, 69.41; H, 7.83; N, 2.63. Found: C, 69.06; H. 7.87; N, 2.51.

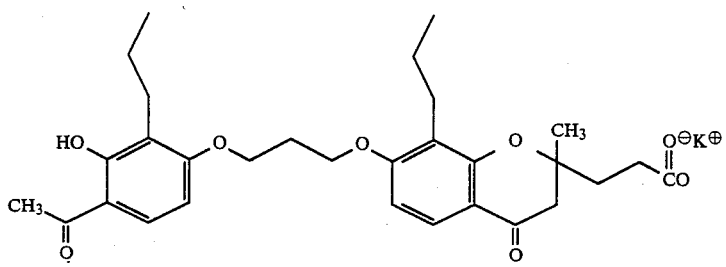

EXAMPLE 22

3-[7-[3-(4-acetyl-3-hydroxy-2-propylphenoxy)propoxy]-3,4-dihydro-2-methyl-4-oxo-8-propyl-2H-1-benzopyran-2-yl]propanoic acid, monopotassium salt A solution of 0.13 g (1.9 mmole) of 85% potassium hydroxide in 25 ml of methanol was added to a solution of 1.0 g (1.8 mmole) of the title compound of Example 7 in 25 ml of methanol. The solution was neutralized with a sulfonic acid-type cation exchange resin, filtered, and evaporated to dryness. The residue was triturated with diethyl ether to give 0.7 g of the title compound. Structure assignment was confirmed by elemental analysis.

Analysis. Calcd. for $C_{30}H_{37}O_8K.3/2H_2O$: C, 60.89; H, 6.81; K, 6.61. Found: C, 61.08; H, 6.71; K, 6.69.

ml (1.5 mmole) of triethanolamine. The solvent was evaporated and the residue was triturated with ether to give a solid. Recrystallization from ether/hexane gave 0.6 g of the title compound, mp. 84°-85°. Structure assignment was confirmed by nmr and infrared spectra and by elemental analysis.

IR(CHCl$_3$): 1620, 1670, 1700, 1740 cm$^{-1}$.

Analysis. Calcd. for $C_{36}H_{53}O_{11}N$: C, 63.98; H, 7.91; N, 2.07. Found: C, 63.86; H. 8.01; N, 1.98.

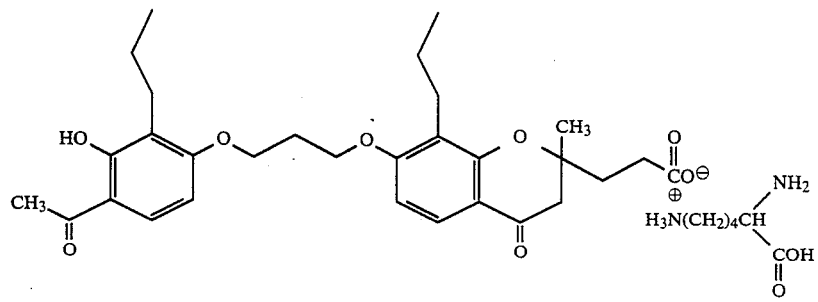

EXAMPLE 34

3-[7-[3-(4-acetyl-3-hydroxy-2-propylphenoxy)propoxy]-3,4-dihydro-2-methyl-4-oxo-8-propyl-2H-1-benzopyran-2-yl]propanoic acid, 5-amino-5-carboxypentanaminium salt The title compound, mp. 125°-127°, was prepared by the method of Example 23 using 0.98 g (1.8 mmole) of the title compound of Example 7 and 0.24 g (1.6 mmole) of DL-lysine as starting materials. Structure assignment was confirmed by nmr and infrared spectra and by elemental analysis.

IR(KBr): 1635, 1685 cm$^{-1}$.

Analysis: Calcd. for $C_{36}H_{52}O_{10}.\frac{1}{2}H_2O$: C, 66.42; H, 7.84; N, 4.11. Found: C, 63.43; H, 7.79; N, 4.09.

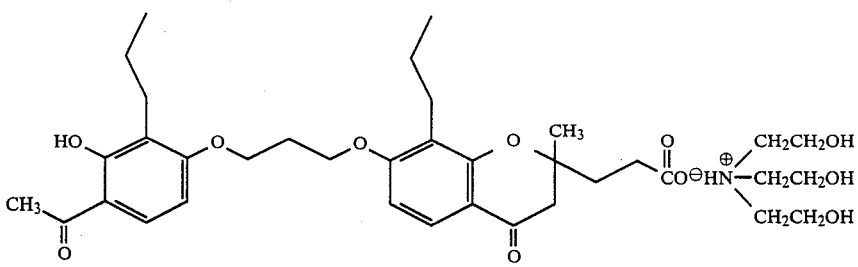

EXAMPLE 23

3-[7-[3-(4-acetyl-3-hydroxy-2-propylphenoxy)propoxy]-3,4-dihydro-2-methyl-4-oxo-8-propyl-2H-1-benzopyran-2-yl]propanoic acid, tris(hydroxyethyl)ammonium salt To a solution of 0.8 g (1.5 mmole) of the title compound of Example 7 in 25 ml of methanol was added 0.2

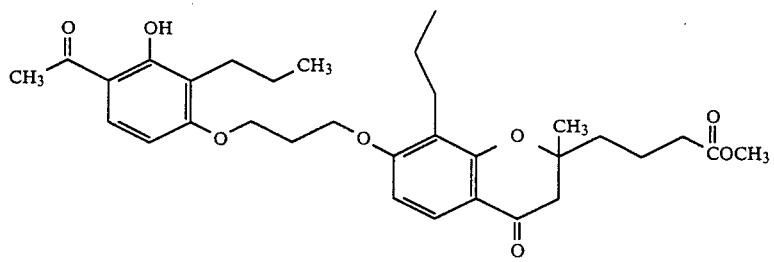

EXAMPLE 25

Methyl 4-[7-[3-(4-acetyl-3-hydroxy-2-propylphenoxy)propoxy]-3,4-dihydro-2-methyl-4-oxo-8-propyl-2H-1-benzopyran-2-yl]butanoate The title compound was prepared by the methods of Examples 1 and 6 using methyl 5-oxohexanoate as starting material. Structure assignment was confirmed by nmr and infrared spectra and by elemental analysis.

IR(CHCl$_3$): 1625, 1675, 1730 cm$^{-1}$.

Analysis. Calcd. for C$_{32}$H$_{42}$O$_8$: C, 69.29; H, 7.63. Found: C, 68.80; H, 7.72.

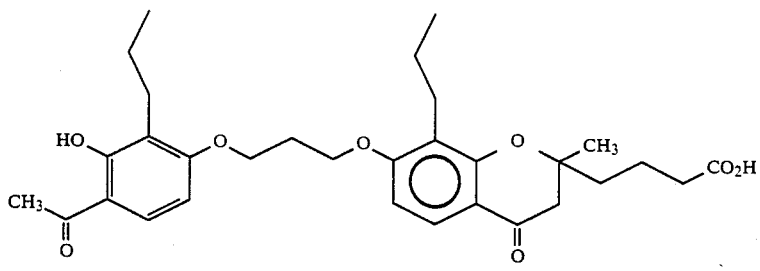

EXAMPLE 26

4-[7-[3-(4-acetyl-3-hydroxy-2-propylphenoxy)propoxy]-3,4-dihydro-2-methyl-4-oxo-8-propyl-2H-1-benzopyran-2-yl]butanoic acid The title compound, mp. 106°–108°, was prepared by the method of Example 7 using the title compound of Example 25 as starting material. Structure assignment was confirmed by nmr and infrared spectra and by elemental analysis.

IR(CHCl$_3$): 1625, 1675, 1710, 1750 cm$^{-1}$.

Analysis. Calcd. for C$_{31}$H$_{40}$O$_8$: C, 68.87; H, 7.46. Found: C, 68.68; H, 7.79.

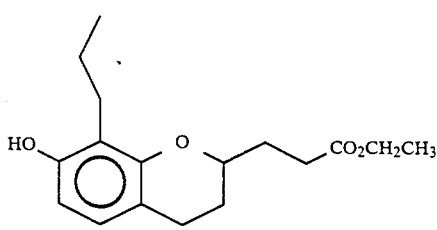

EXAMPLE 27 ethyl 3-(3,4-dihydro-7-hydroxy-8-propyl-2H-1-benzopyran-2-yl)propanoate

A solution of 2.0 g (5.1 mmole) ethyl 3-(4-oxo-7-phenylmethoxy-8-propyl-4H-1-benzopyran-2-yl)-2-propenoate in 40 ml of acetic acid was hydrogenated at 50 psi and 70° over 5% palladium on carbon catalyst. The catalyst was removed by filtration and the filtrate was evaporated to dryness to give 1.3 g of the title compound as an oil. Structure assignment was supported by nmr and infrared spectra.

nmr (CDCl$_3$): δ(ppm) 0.95 (t, J=7 Hz, 3H, propyl CH$_3$); 1.27 (t, J=7 Hz, 3H, ester CH$_3$); 3.9 (m, b 1H, 2-proton); 4.13 (q, J=7 Hz, 2H, ester CH$_2$); 6.29, 6.69 (pair d, aromatic).

IR(CHCl$_3$): 1725 cm$^{-1}$.

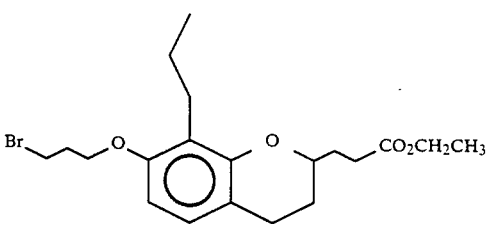

EXAMPLE 28 ethyl 3-[7-(3-bromopropoxy)-3,4-dihydro-8-propyl-2H-1-benzopyran-2-yl]propanoate The title compound was prepared by the method of Example 11 using the product of Example 27 as starting material. Structure assignment was supported by nmr and infrared spectra.

nmr (CDCl$_3$): additional signals include δ(ppm) 3.59 (t, J=7 Hz, 2H, CH$_2$Br) (compare Example 27).

IR(CHCl$_3$): 1725 cm$^{-1}$.

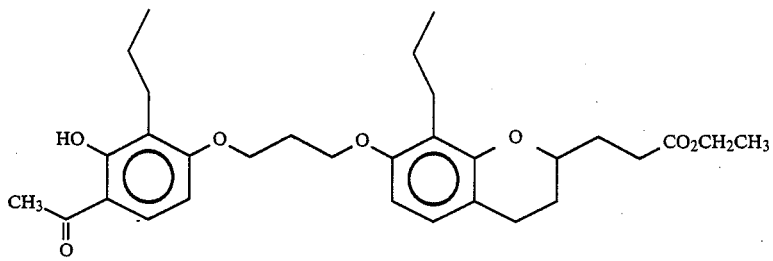

EXAMPLE 29 ethyl 3-[7-[3-(4-acetyl-3-hydroxy-2-propylphenoxy)propoxy]-3,4-dihydro-8-propyl-2H-1-benzopyran-2-yl]propanoate The title compound, mp. 68°–70°, was prepared by the method of Example 6 using the product of Example 28 as starting material. Structure assignment was confirmed by nmr and infrared spectra and by elemental analysis.

nmr (CDCl$_3$): δ(ppm) 0.89 (t, J=7 Hz, 6H, propyl CH$_3$'s); 1.25 (t, J=7 Hz, 3H, ester CH$_3$); 2.27 (t, J=6H, 2H, CH$_2$CH$_2$, CH$_2$); 2.54 (s, 3H, acetyl CH$_3$); 3.9 (m, 1H, 2-proton); 6.39, 6.42, 6.78, 7.54 (sets of d's, aromatic).

IR(CHCl$_3$): 1625, 1725 cm$^{-1}$.

Analysis. Calc. for C$_{31}$H$_{42}$O$_7$: C, 70.70; H, 8.04. Found: C, 70.57; H, 8.09.

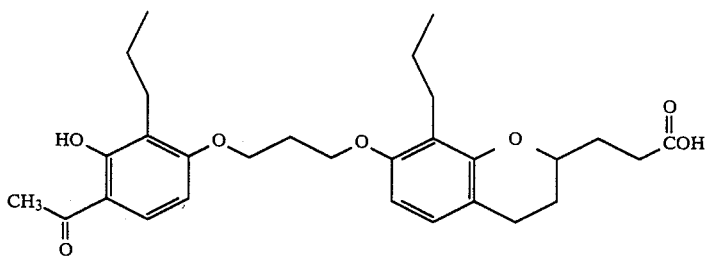

EXAMPLE 30

3-[7-[3-(4-acetyl-3-hydroxy-2-propylphenoxy)propoxy]-3,4-dihydro-8-propyl-2H-1-benzopyran-2-yl]propanoic acid The title compound, mp. 109°–110°, was prepared by the method of Example 7 using the product of Example 29 as starting material. Structure assignment was confirmed by nmr and infrared spectra and by elemental analysis. nmr (CDCl$_3$): loss of ester protons (compare Example 29)

IR(KBr): 1635, 1705 cm$^{-1}$.

Analysis. Calcd. for C$_{29}$H$_{38}$O$_7$: C, 69.86; H, 7.68. Found: C, 69.83; H, 7.68.

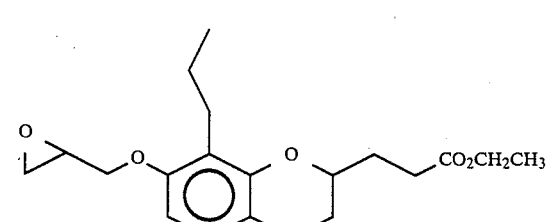

EXAMPLE 31 ethyl 3-[3,4-dihydro-7-(2-oxiranylmethoxy)-8-propyl-2H-1-benzopyran-2-yl]propanoate The title compound was prepared by the method of Example 11 using 3.0 g (10.3 mmole) of the product of Example 27 and 1.3 ml (15 mmole) of epibromohydrin as starting materials. Structure assignment was supported by nmr and infrared spectra.

IR(CHCl$_3$): 1725 cm$^{-1}$.

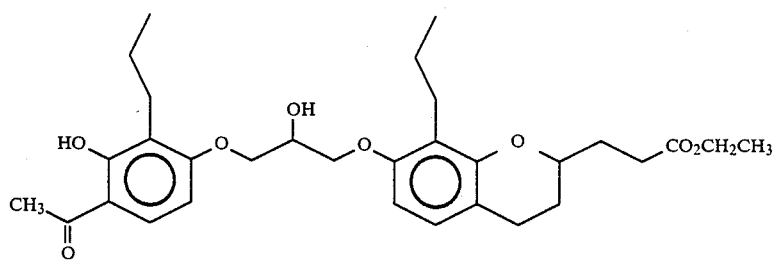

EXAMPLE 32 ethyl 3-[7-[3-(4-acetyl-3-hydroxy-2-propylphenoxy)-2-hydroxypropoxy]-3,4-dihydro-8-propyl-2H-1-benzopyran-2-yl]propanoate To a solution of 2.9 g (8.3 mmole) of the title compound of Example 31 and 2.4 g (12.5 mmole) of 2,4-dihydroxy-3-propylacetophenone in 30 ml of dry dimethylformamide was added two drops of Triton B. The reaction mixture was heated at 110°–120° for 48 hours, then cooled and evaporated to dryness. Chromatography of the crude material on silica gel using 20% acetone/hexane as eluent gave 1.6 g of product as an oil. Structure assignment was supported by nmr and infrared spectra.

nmr (CDCl$_3$): δ(ppm) 0.91, 0.93 (pair t, 6H, propyl CH$_3$'s); 1.25 (t, J=7 Hz, 3H, ester CH$_3$); 2.56 (s, 3 Hz, acetyl CH$_3$); 3.90, (m, 1H, CHOH); 4.12 (d, J=7 Hz, 4H, OCH$_2$'s); 6.40, 6.43, 6.80, 7.56 (sets of d's, aromatic)
IR(CHCl$_3$): 1625, 1725 cm$^{-1}$.

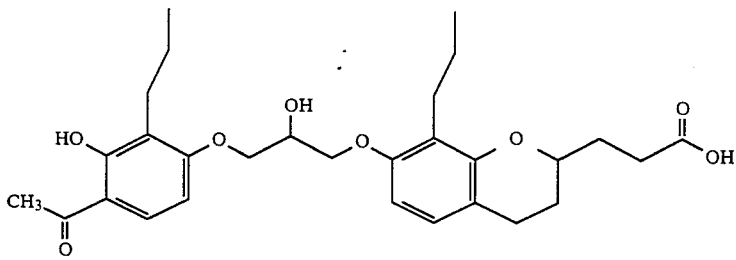

EXAMPLE 33

3-[7-[3-(4-acetyl-3-hydroxy-2-propylphenoxy)-2-hydroxypropoxy]-3,4-dihydro-8-propyl-2H-1-benzopyran-2-yl]propanoic acid The title compound was prepared by the method of Example 7 using the ester product of Example 32 as starting material. Structure assignment was confirmed by nmr and infrared spectra and by elemental analysis.

nMr (CDCl$_3$): loss of ester protons (compare Example 32).

IR(CHCl$_3$): 1625, 1705 cm$^{-1}$.

Analysis. Cald. for C$_{29}$H$_{38}$O$_8$: C, 67.68; H, 7.44. Found: C, 67.03; H, 7.39.

EXAMPLE 34 methyl 7-hydroxy-4-oxo-8-propyl-4H-1-benzopyran-2-oate

To a solution of 99.7 g (0.513 mole) of 2,4-dihydroxy-3-propylacetophenone and 72.7 g (0.77 mole) of dimethyl oxalate in 1 liter of dry dimethylformamide was added in portions 97 g (1.8 mmole) of sodium methoxide. After stirring for 4 hours, 1.8 l of acetic acid was added and stirring was continued for 4 days. The reaction mixture was heated in a steam bath for four hours and evaporated to dryness. Water was added to the residue and the mixture was heated to boiling. A solid was filtered off and recrystallized from ethanol to give 89.8 g of the title compound, mp. 222°–224°. Structure assignment was supported by nmr and infrared spectra.

IR(KBr): 1650, 1745 cm$^{-1}$

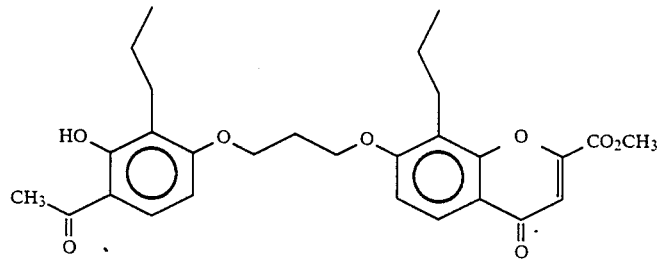

EXAMPLE 35 methyl 7-[3-(4-acetyl-3-hydroxy-2-propylphenoxy)propoxy]-4-oxo-8-propyl-4H-1-benzopyran-2-oate The title compound was prepared by the method of Example 6 using the product of Example 34 as starting material. Structure assignment was confirmed by nmr and infrared spectra.

nrm (CDCl$_3$): δ(ppm) 0.89, 0.93 (pair t, 6H, propyl CH$_3$'s); 2.55 (s, 3H, acetyl CH$_3$); 2.62, 2.88 (pair t, 4, OCH₂'s); 6.98 (s, 1H, C=CH); 6.42, 7.00, 7.54, 8.00 (sets of d's, aromatic).

IR(CHCl₃): 1650, 1745 cm⁻¹.

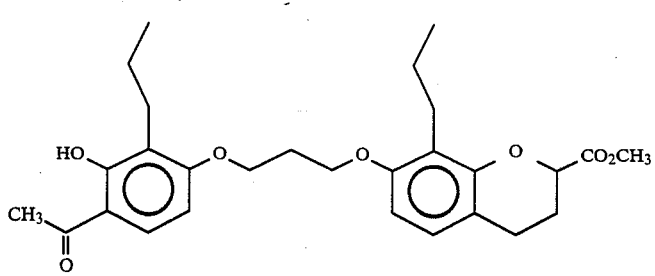

EXAMPLE 36 methyl 7-[3-(4-acetyl-3-hydroxy-2-propylphenoxy)propoxy]-3,4-dihydro-8-propyl-2H-1-benzopyran-2-oate The title compound was prepared by the method of Example 27 using 30.7 g (61.9 mmole) of the product of Example 35 as starting material. Structure assignment was supported by nmr and infrared spectra.

nmr (CDCl₃): loss of alkenyl proton, addition of 2-proton at δ(ppm) 4.41 (t, J=5 Hz) (compare Example 35)

IR(CHCl₃): 1610, 1620, 1730, 1750 cm⁻¹.

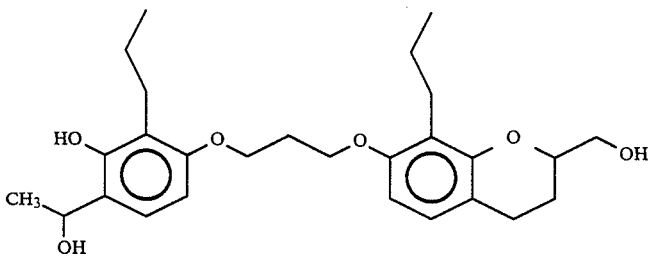

EXAMPLE 37

7-[3-(3-hydroxy-4-(1-hydroxyethyl)-2-propylphenoxy)-propoxy]-3,4-dihydro-8-propyl-2H-1-benzopyran-2-ylmethanol A solution of 2.8 g (0.13 mole) of lithium borohydride in 500 ml of tetrahydrofuran was added to a solution of 25.0 g (51.6 mmole) of the title compound of Example 36 in 200 ml of tetrahydrofuran. The reaction mixture was stirred at room temperature for two hours and heated to reflux for one hour. After cooling the mixture, the excess borohydride reagent was destroyed by the addition of water and then a small amount of dilute hydrochloric acid. The reaction mixture was diluted with ethyl acetate and washed successively with sodium bicarbonate solution, water and brine, dried over MgSO₄, filtered, and evaporated to dryness. Chromatography of the residue on silica gel using 40% ethyl acetate/hexane as eluent gave 16.5 g of the title compound as an oil. Structure assignment was supported by nmr and infrared spectra.

nmr (CDCl₃): loss of ester CH₃, change in acetyl CH₃ to δ(ppm) 1.55 (d, J=7 Hz); additional signal at 4.96 (q, J=6 Hz, 1H, methyl-CHO-) (compare Example 36).

IR(CHCl₃): no carbonyl band between 1600 and 1800 cm⁻¹

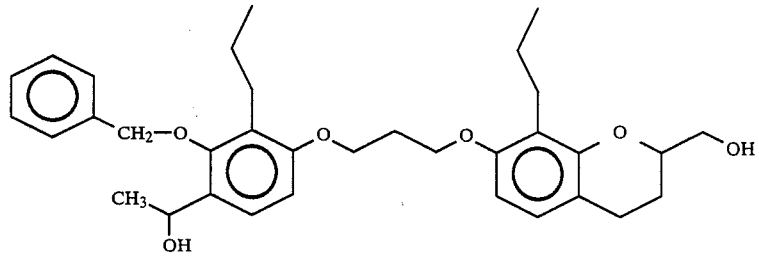

EXAMPLE 38

7-[3-(4-(1-hydroxyethyl)-3-(phenylmethoxy)-2-propylpenoxy)propoxy]-3,4-dihydro-8-propyl-2H-1-benzopyran-2-ylmethanol The title compound was prepared by the general method of Example 11 using the product of Example 37 and benzyl chloride as starting materials. Structure assignment was supported by nmr and infrared spectra.

IR(CHCl₃): no carbonyl band between 1600 and 1800 cm⁻¹.

nmr (CDCl₃): additional aromatic protons (compare Example 37).

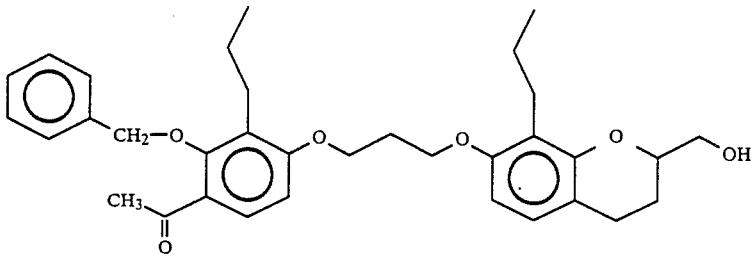

EXAMPLE 39

7-[3-(4-acetyl-3-(phenylmethoxy)-2-propylphenoxy)-propoxy]-3,4-dihydro-8-propyl-2H-1-benzopyran-2-ylmethanol To a solution of 8.9 g (16.2 mmole) of the title compound of Example 38 in 150 ml of methylene choride was added 18 g (162 mmole) of manganese dioxide. The reaction mixture was stirred at room temperature for 12 hours and filtered. Removal of the solvent gave 6.9 g of the title compound, mp. 83°–85°. Structure assignment was supported by nmr and infrared spectra.

IR(CHCl$_3$): 1665 cm$^{-1}$.

nmr (CDCl$_3$): reappearance of acetyl CH$_3$ at δ(ppm) 2.55 (s, 3H) (compare Examples 36, 37, 38)

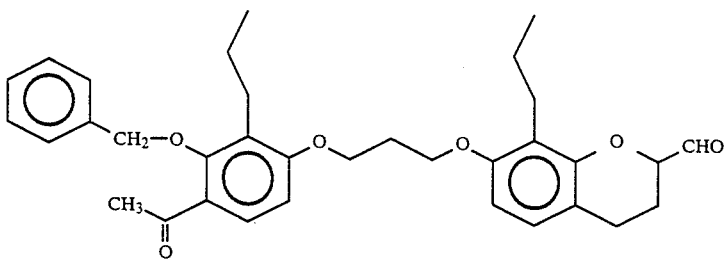

EXAMPLE 40

7-[3-(4-acetyl-3-(phenylmethoxy)-2-propyl phenoxy)propoxy]-3,4-dihydro-8-propyl-2H-1-benzopyran-2-carboxaldehyde A solution of 1.2 ml (13.3 mmole) of oxalyl chloride in 30 ml of methylene chloride was cooled to −70°, and a solution of 1.9 ml (26.6 mmole) of dimethylsulfoxide in 9 ml of methylene chloride was added. The mixture was stirred for 5 minutes and a solution of 6.6 g (12.1 mmole) of the title compound of Example 39 in 20 ml of methylene chloride was added. After stirring an additional 15 minutes, 8.5 ml (60.5 mmole) of triethylamine was added, and the mixture was stirred at −70° for 5 minutes and allowed to warm to room temperature. Water was added and the layers were separated. The organic layer was washed successively with dilute hydrochloric acid, 5% sodium bicarbonate solution, water and brine, dried over MgSO$_4$, and filtered. Removal of the solvent gave 6.44 g of the title compound as a yellow oil. Structure assignment was supported by nmr and infrared spectra.

nmr (CDCl$_3$): δ(ppm) 9.76 (s, 1H, CHO).
IR(CHCl$_3$): 1665, 1735 cm$^{-1}$.

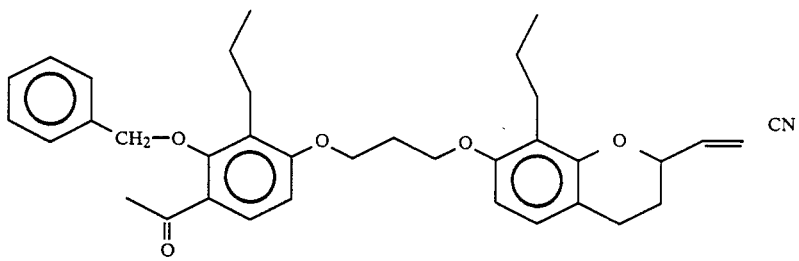

EXAMPLE 41

3-[7-[3-(4-acetyl-3-(phenylmethoxy)-2-propylphenoxy)-propoxy]-3,4-dihydro-8-propyl2H-1-benzopyran-2yl]-2(E and Z)propenenitrile To a solution of 6.35 (11.7 mmole) of the title compound of Example 40 in 150 ml of benzene was added 4.04 g (13.5 mmole) of cyanomethylenetriphenylphosphorane. The reaction mixture was stirred for 12 hours at room temperature and evaporated to dryness. Chromatography of the residue on silica gel using 20% ethyl acetate/hexane as eluent gave 1.3 g of the cis isomer, 0.8 g of the trans isomer and 1.1 g of a 53:47 cis/trans mixture. Structure assignment was supported by nmr and infrared spectra.

nmr (CDCl$_3$) (cis isomer): δ(ppm) 5.44 (dd, J$_1$=11 Hz, J$_2$=1.5 Hz, 1H, CHCN) (trans isomer): δ(ppm) 5.69 (dd, J$_1$=16 Hz, J$_2$=3 Hz 1H, CHCN); 6.77 (dd, J$_1$=16 Hz, J$_3$=4 Hz, 1H, HC=C—CN).

IR(CHCl₃) (cis isomer): 1665, 2210 cm⁻¹, (trans isomer): 1665, 2230 cm⁻¹.

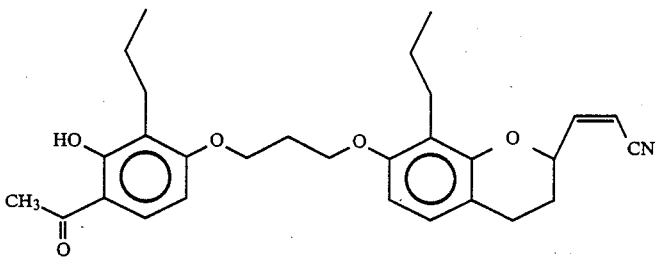

EXAMPLE 42

3-[7-[3-(4-acetyl-3-hydroxy-2-propylphenoxy)propoxy]-3,4-dihydro-8-propyl-2H-1-benzopyran-2-yl]-2(Z)-propenenitrile To 1.4 g (2.4 mmole) of the cis isomer product of Example 41 in 70 ml of methylene chloride cooled to −78°, was added 9.7 ml (9.6 mmole) of a 1M solution of boron trichloride in methylene chloride. After addition was complete, the reaction was poured onto an ice/water mixture and additional methylene chloride was added. The organic layer was washed with and brine, dried over MgSO₄, and filtered. Removal of the solvent gave 1.13 g of the title compound as an oil. Structure assignment was supported by nmr and infrared spectra.

nmr (CDCl₃): δ(ppm) 5.46 (dd, J₁=11 Hz, 1H, CHCN); 6.67 (dd, J₁=11 Hz, J₃=3.5 Hz, 1H, HC=C—CN); loss of ester protons (compare Example 41).

IR(CHCl₃): 1625, 2230 cm⁻¹.

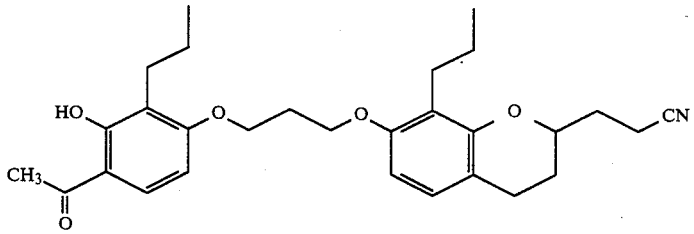

EXAMPLE 43

3-[7-[3-(4-acetyl-3-hydroxy-2-propylphenoxy)propoxy]-3,4-dihydro-8-propyl-2H-1-benzopyran-2-yl]propanenitrile A solution of 1.6 g (3.4 mmole) of the title compound of Example 42 in 27 ml of ethyl acetate and 3 ml of acetic acid was hydrogenated at atmospheric pressure and room temperature using 10% palladium on carbon catalyst. The catalyst was removed by filtration and the filtrate was evaporated to dryness. Chromatography of the residue on silica gel using 20% ethyl acetate/hexane as eluent gave 1.3 g of the title compound, mp. 89°–89.5°. Structure assignment was confirmed by nmr and infrared spectra and by elemental analysis.

nmr (CDCl₃): loss of alkenyl protons (compare Example 41).

IR(CHCl₃): 1625, 2250, cm⁻¹.

Analysis. Calcd. for C₂₉H₃₇O₅N: C, 72.62; H, 7.78; N, 2.92. Found: C, 72.92; H, 7.79; N, 2.85.

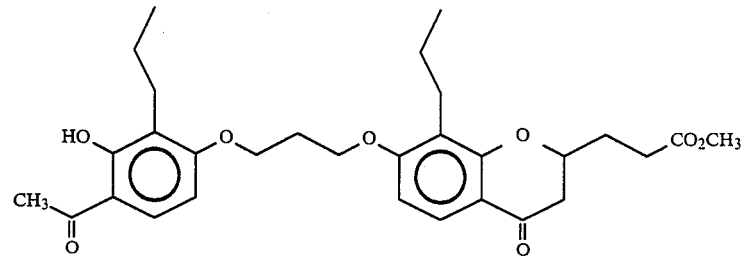

EXAMPLE 44 methyl 3-[7-[3-(4-acetyl-3-hydroxy-2-propylphenoxy)propoxy]-3,4-dihydro-4-oxo-8-propyl-2H-1-benzopyran-2-yl]propanoate A solution of 1.9 g (3.6 mmole) of methyl 3-[7-[3-(4-acetyl-3-hydroxy-2-propylphenoxy)propoxy]-4-oxo-8-propyl-3H-1-benzopyran-2-yl]propanoate in 20 ml of ethanol and 20 ml of tetrahydrofuran was hydrogenated at room temperature and 2 psi using Raney nickel catalyst. The reaction mixture was filtered and evaporated to dryness. Chromatography of the crude material on silica gel using 4% acetone/toluene as eluent afforded 0.9 g of the title compound, mp. 101°–101.5°. Structure assignment was confirmed by nmr and infrared spectra and by elemental analysis.

IR(CHCl₃): 1625, 1675, 1730 cm⁻¹.

Analysis. Calcd. for $C_{30}H_{38}O_8$: C, 68.42; H, 7.27.
Found: C, 68.30; H, 7.22.

IR(KBr): 1635, 1665, 1725 cm$^{-1}$.
Analysis. Calcd. for $C_{29}H_{36}O_8$: C, 67.95; H, 7.07.

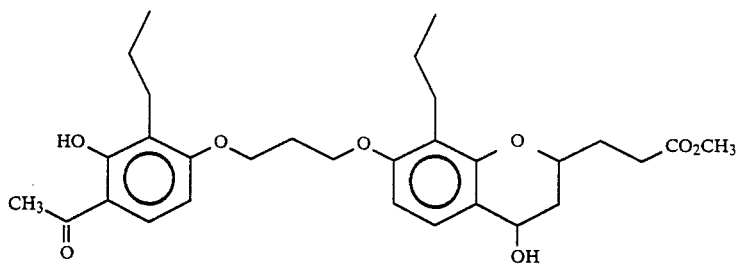

Found: C, 67.73; H, 7.05.

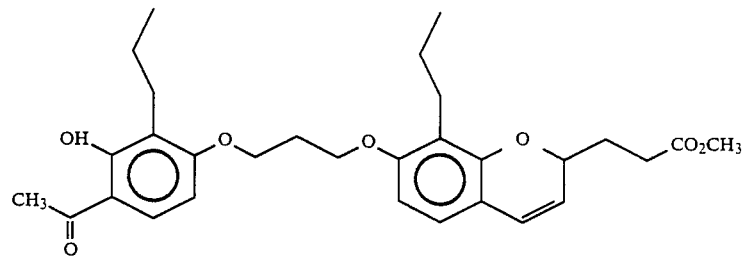

EXAMPLE 45 methyl 3-[7-[3-(4-acetyl-3-hydroxy-2-propylphenoxy)propoxy]-3,4-dihydro-4-hydroxy-8-propyl-2H-1-benzopyran-2-yl]propanoate Other chromatographic fractions of Example 44 afforded 1.0 g of the title alcohol, m.p. 125°–125.5°. Structure assignment was confirmed by nmr and infrared spectra and by elemental analysis.

IR(CHCl$_3$): 1630, 1735 cm$^{-1}$.
Analysis. Calcd. for $C_{30}H_{40}O_8$: C, 68.16; H, 7.63.
Found: C, 68.21; H, 7.60.

EXAMPLE 47 methyl 3-[7-[3-(4-acetyl-3-hydroxy-2propylphenoxy)propoxy]-8-propyl-2H -1benzopyran-2-yl]propanoate As solution of 0.2 g (2.4 mmole) of methanesulfonyl chloride in 5 ml of methylene chloride was added dropwise to a cooled (−20°) solution of 1.0 g (2.0 mmole) of the hydroxy product of Example 45 and 0.7 ml (5 mmole) of triethylamine in 20 ml of methylene chloride. The reaction mixture was cooled at −5° for 16 hours, then poured onto ice and extracted with diethyl ether.

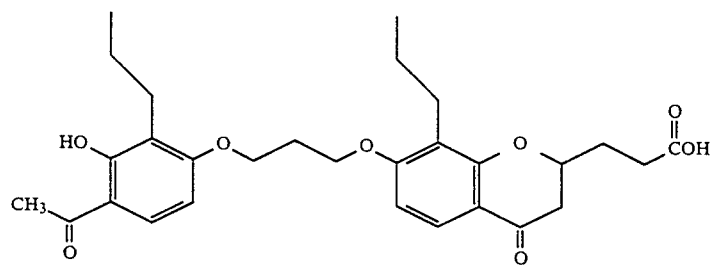

EXAMPLE 46

3-[7-[3-(4-acetyl-3-hydroxy-2-propylphenoxy)-propoxy]-3,4-dihydro-4-oxo-8-propyl2H-1-benzopyran-2-yl]propanoic acid The title compound, mp. 149°–150°, was prepared by the method of Example 7 using the ketone product of Example 44 as starting material. Structure assignment was confirmed by nmr and infrared spectra and by elemental analysis.

The organic layer was washed successively with 2M hydrochloric acid, 10% sodium bicarbonate solution and water, then dried over MgSO$_4$ and filtered. Removal of the solvent gave 0.6 g of the title compound as an oil. Structure assignment was confirmed by nmr and infrared spectra.

nmr (CDCl$_3$): δ(ppm) 3.64 (s, 3H, ester CH$_3$); 4.8 (m, 1H, 2-proton); 5.5 (dd, J$_1$=10 Hz, 1H, 3-proton) 6.75 (dd, J$_1$=10 Hz, 1H, 4-proton).

IR(CHCl$_3$): 1605, 1625, 1745 cm$^{-1}$.

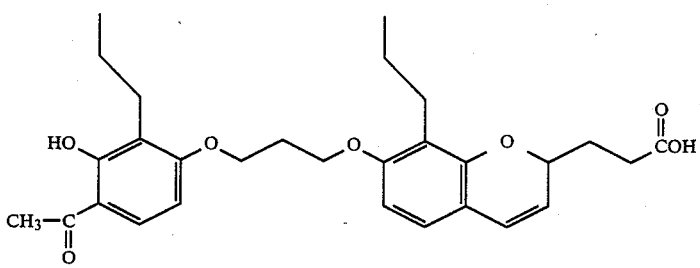

EXAMPLE 48

3-[7-[3-(4-acetyl-3-hydroxy-2-propylphenoxy)propoxy]-8-propyl-2H-1-benzopyran2-yl]propanoic acid The title compound, mp. 60°-62°, was prepared by the method of Example 7 using the product of Example 47 as starting material. Structure assignment was confirmed by nmr and infrared spectra and by elemental analysis.

nmr (CDCl$_3$): δ(ppm) 5.58 (dd, J$_1$=10 Hz, J$_2$=3 Hz, 1H, 3-proton); 6.37 (dd, J$_1$=10 Hz, J$_3$=1.5 Hz, 1H, 4-proton); loss of ester CH$_3$.
IR(KBr): 1605, 1625, 1725, 1730 cm$^{-1}$.
Analysis. Calcd. for C$_{29}$H$_{36}$O$_7$: C, 70.14; H, 7.31. Found: C, 69.94; H, 7.11.

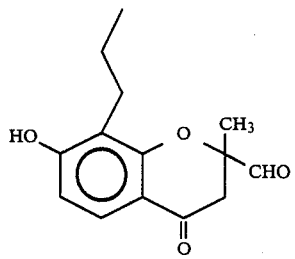

EXAMPLE 49

3,4-dihydro-7-hydroxy-2-methyl-4-oxo-8-propyl-2H-2-benzopyran-2-carboxaldehyde

A solution of 30.0 g of 2,4-dihydroxy-3-propylacetophenone in 125 ml of toluene containing 15.5 ml of pyrrolidine was heated at reflux using a Dean-Stark trap to remove water. After 29.2 ml of pyruvaldehyde dimethyl acetal was added to the cooled (ca. 0°) solution, the mixture was heated to reflux as additional water was removed. After five hours an additional 5.2 ml of pyrrolidine was added and the mixture was refluxed a further 18 hours. The reaction mixture was cooled, concentrated, and taken up in ethyl acetate. The resultant solution was washed sequentially with water, 1N hydrochloric acid, and brine, dried over magnesium sulfate, filtered, and concentrated to dryness. The residue was dissolved in ethyl acetate/hexane, filtered through silica gel, and concentrated to an oil which was purified by column chromatography on silica gel. The intermediate acetal derivative of the title compound was collected as a yellow solid (13.7 g) which was used without further purification to prepare the title compound. (An analytically pure sample, m.p. 146°-148°, was recrystallized from ethyl acetate/hexane.) A solution of 2.0 g of the intermediate acetal in 20 ml of acetic acid containing 10 ml of 10% sulfuric acid was heated at 80° for three hours. The mixture was taken up in ethyl acetate, washed with water, aqueous sodium bicarbonate, and brine, then dried with magnesium sulfate, filtered, and concentrated. The title compound, isolated as 1.7 g of an oil, was used in subsequent reactions without further purification. Structure assignment was supported by nmr and infrared spectra.

nmr (CDCl$_3$): δ(ppm) 0.99, 1.55, 2.70 (t, m, t, 7H, propyl protons); 1.53 (s, 3H, methyl); 2.88 (g, 2H, ring CH$_2$); 6.52, 7.62 (pair d, aromatic); 9.60 (s, 1H, CHO).
IR (CHCl$_3$): 1740, 1675 cm$^{-1}$.

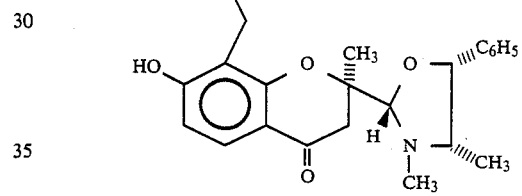

EXAMPLE 50

2R-(3,4S-dimethyl-5R-phenyl-2S-oxazolidinyl)-3,4-dihydro-7-hydroxy-2-methyl-8-propyl-2H-1-benzopyran-4-one A solution of 20.0 g of the title compound of Example 49 and excess 1-ephedrine in 150 ml of benzene was heated at reflux using a Dean-Stark trap to remove water. After four hours at reflux the solution was filtered through silica gel, washing with 50% by volume ethyl acetate/hexane, and then concentrated to dryness in vacuo. Column chromatography on silica gel using ethyl acetate/hexane, after recycling to obtain only the least polar component, afforded 1.1 g of the title compound, m.p. 196°-197°. Structure determination was confirmed by X-ray crystallography.

[α]$_D$ −2.1° (1.029% in acetone).

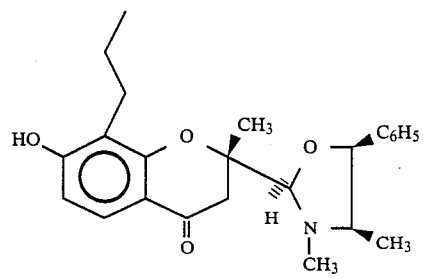

EXAMPLE 51

2S-(3,4R-dimethyl-5S-phenyl-2R-oxazolidinyl)-3,4-dihydro-7hydroxy-2-methyl8propyl-2H-1-benzopyran-4-one The title compound (4.85 g), m.p. 196°-198°, was prepared by the method of Example 50 using 17 g of the title compound of Example 49 and excess d-ephedrine. The optical rotation of the title compound was opposite in sign to that for the title product of Example 50.

$[\alpha]_D + 1.6°$ (1.014% in acetone).

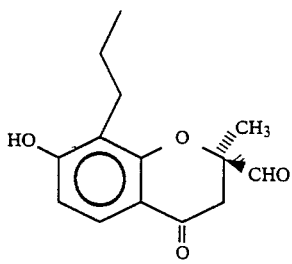

EXAMPLE 52

3,4-dihydro-7-hydroxy-2-methyl-4-oxo-8-propyl-2H-1-benzopyran-2R-carboxaldehyde

The title compound of Example 50 (4.1 g) was dissolved in 150 ml of methanol to which was then added 12 g of Dowex-50 (H+ form) and 50 ml of water. After 2.5 hours at 50° the mixture was filtered and the filtrate concentrated in vacuo to give 1.2 g of the title compound. A second crop of the product was obtained by suspending the recovered exchange resin in 100 ml of 90% aqueous methanol, adding an additional 4 g of Dowex-50, heating at 60° for three hours, filtering, and concentrating to dryness. A total of 2.4 g of aldehyde product was obtained. The (R)-aldehyde was used for subsequent reactions without further purification.

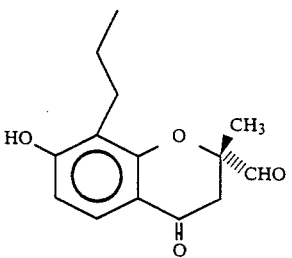

EXAMPLE 53

3,4-dihydro-7-hydroxy-2-methyl-4-oxo-8-propyl-2H-1-benzopyran-2S-carboxaldehyde

The title compound (3.05 g) was prepared by the method of Example 52 using 5.0 g of the title compound of Example 51. The (S)-aldehyde was used for subsequent reactions without further purification.

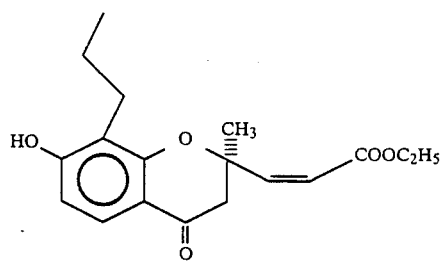

EXAMPLE 54 ethyl 3-(3,4-dihydro-7-hydroxy-2R-methyl-4-oxo-8-propyl-2H-1-benzopyran-2-yl)-2(Z)-propenoate A solution of 1.2 g of the (R)-aldehyde product of Example 52 and 1.8 g of (carbethoxymethylene)triphenylphosphorane was allowed to stand for about seven hours. The solution was filtered through silica gel and the filtrate concentrated to dryness. The residue was then chromatographed on silica gel using 18% ethyl acetate/hexane as eluent. Early chromatographic fractions afforded the title compound (i.e., the cis isomer), m.p. 104°-106°.

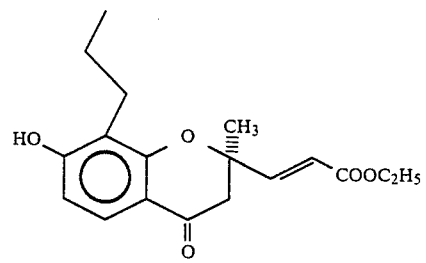

EXAMPLE 55 ethyl 3-(3,4-dihydro-7-hydroxy-2R-methyl-4-oxo-8-propyl-2H-1-benzopyran-2-yl)-2(E)-propenoate Later chromatographic fractions of Example 54 afforded the trans isomer, m.p. 111.5°-112.5°. Structure assignment was supported by nmr spectra, optical rotation, and elemental analysis.

nmr (CDCl$_3$): alkenyl protons at $\delta$(ppm) 6.00 (d, J=16 Hz), 6.93 (d, J=16 Hz).

$[\alpha]_D + 129.0°$ (0.903% in CHCl$_3$).

Analysis. Calcd. for $C_{18}H_{22}O_5 \cdot \frac{1}{2}H_2O$: C, 66.96; H, 7.02. Found: C, 67.08; H, 6.95.

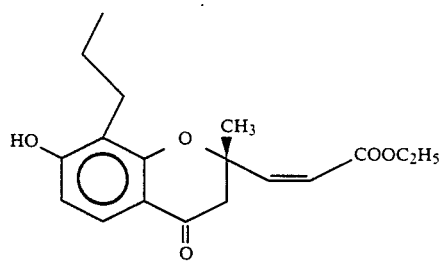

EXAMPLE 56

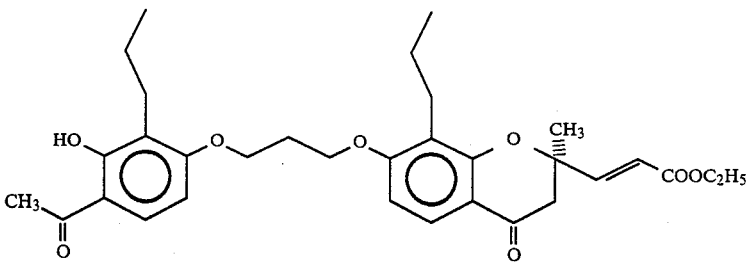

Analysis. Calcd. for $C_{18}H_{22}O_5$: C, 67.91; H, 6.97. Found: C, 67.67; H, 6.98.

ethyl 3-(3,4-dihydro-7-hydroxy-2S-methyl-4-oxo-8-propyl-2H-1-benzopyran-2-yl)-2(Z)-propenoate The title compound (i.e., the cis isomer), m.p. 109°-110°, was prepared by the method of Example 54 using 3.05 g of the (S)-aldehyde product of Example 53 and 4.7 g of the phosphorane reagent. Structure assignment was supported by optical rotation and elemental analysis.

$[\alpha]_D$ —185.8° (0.771% in $CHCl_3$)

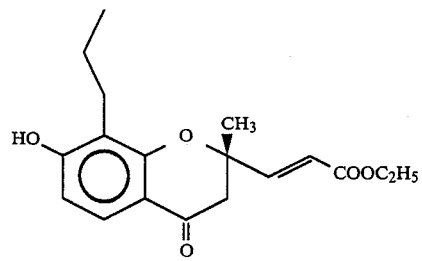

EXAMPLE 57 ethyl 3-(3,4-dihydro-7-hydroxy-2S-methyl-4-oxo-8-propyl-2H-1-benzopyran-2-yl)-2(E)-propenoate Later chromatographic fractions of Example 56 afforded the trans isomer, m.p. 110.5°-111.5°. Structure assignment was supported by optical rotation, and elemental analysis.

$[\alpha]_D$—125.7° (1.015% in $CHCl_3$).

EXAMPLE 58 ethyl 3-[7-[3-(4-acetyl-3-hydroxy-2-propylphenoxy)propoxy]-3,4-dihydro-2R-methyl-4-oxo-8-propyl-2H-1-benzopyran-2-yl)-2(E)-propenoate A mixture of 1.1 g of the title compound of Example 55, 1.0 g of the title compound of Example 5, and 0.91 g of powdered potassium carbonate in 30 ml of dimethylformamide was stirred at room temperature overnight. The reaction mixture was diluted with ethyl acetate and filtered, and the filtrate was washed sequentially with ammonium chloride solution and brine, filtered and concentrated in vacuo to an oil. Column chromatography on silica gel using 7% ethyl acetate/toluene afforded 1.2 g of the title compound, m.p. 135.5°-136.5°. Structure assignment was supported by optical rotation and elemental analysis.

$[\alpha]_D$+91.8° (1.000% in $CHCl_3$).

Analysis. Calcd. for $C_{32}H_{40}O_8$: C, 69.54; H, 7.30. Found: C, 69.32; H, 7.25.

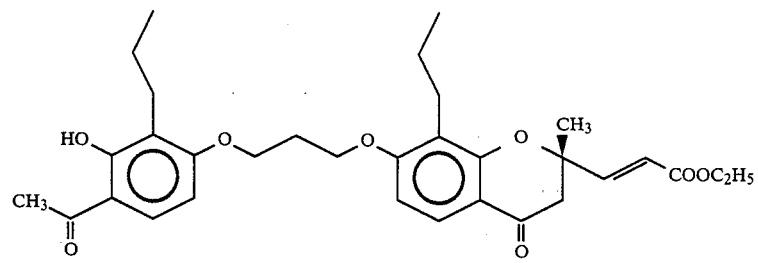

EXAMPLE 59 ethyl 3-[7-[3-(4-acetyl-3-hydroxy-2-propylphenoxy)propoxy]-3,4-dihydro-2S-methyl-4-oxo-8-propyl-2H-1-benzopyran-2-yl)-2(E)-propenoate The title compound, m.p. 134°-135°, was prepared by the method of Example 58 using the title compound of Example 57. Structure assignment was supported by optical rotation and elemental analysis.

$[\alpha]_D$—87.3° (1.002% in $CHCl_3$)

Analysis. Calcd. for $C_{32}H_{40}O_8$: C, 69.54; H, 7.30. Found: C, 69.37; H, 6.96.

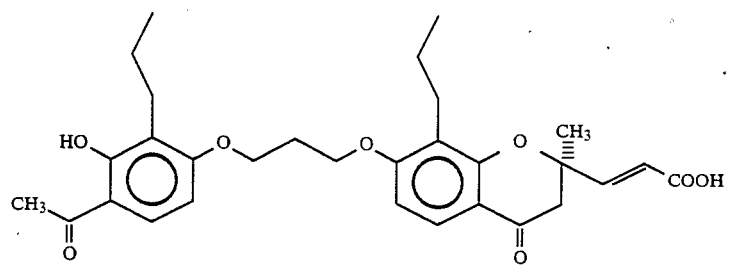

EXAMPLE 60

3-[7-[3-(4-acetyl-3-hydroxy-2-propylphenoxy)propoxy]-3,4-dihydro-2R-methyl-4-oxo-8-propyl-2H-1-benzopyran-2-yl)-2(E)-propenoic acid The title compound, m.p. 179.5°–181°, was prepared from 1.05 g of the ester product of Example 58 using the general method of Example 7, except that the initially formed solid was purified by column chromatography on silica gel (using 85:15:1 toluene/ethyl acetate/acetic acid as eluent), giving 0.67 g of pure solid. Structure assignment was supported by optical rotation and elemental analysis.

$[\alpha]_D +93.3°$ (1.001% in CHCl$_3$).

Analysis. Calcd. for $C_{30}H_{36}O_8$: C, 68.68; H, 6.92. Found: C, 68.62; H, 6.76.

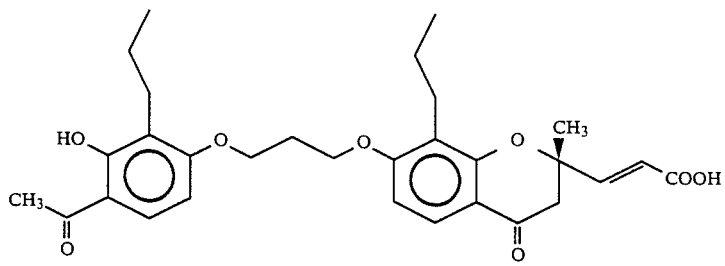

EXAMPLE 61

3-[7-[3-(4-acetyl-3-hydroxy-2-propylphenoxy)-propoxy]-3,4-dihydro-2S-methyl-4-oxo-8-propyl-2H-1-benzopyran-2-yl)-2(E)-propenoic acid The title compound, m.p. 179°–181°, was prepared by the method of Example 60 using 1.1 g of the ester product of Example 59. Structure assignment was supported by optical rotation and elemental analysis.

$[\alpha]_D -90.8°$ (1.002% in CHCl$_3$).

Analysis. Calcd. for $C_{30}H_{36}O_8$: C, 68.68; H, 6.92. Found: C, 68.60; H, 6.79.

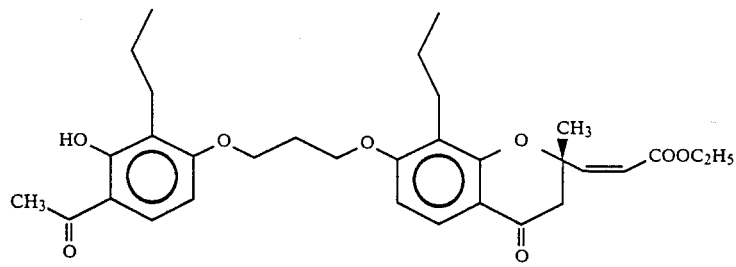

EXAMPLE 62 ethyl 3-[7-[3-(4-acetyl-3-hydroxy-2-propylphenoxy)propoxy]-3,4-dihydro-2S-methyl-4-oxo-8-propyl-2H-benzopyran-2-yl)-2(Z)-propenoate The title compound m.p. 98°–99°, was prepared by the method of Example 58 using the title compound of Example 56. Structure assignment was supported by optical rotation and elemental analysis.

$[\alpha]_D -118.8°$ (1.013% in CHCl$_3$).

Analysis. Calcd. for $C_{32}H_{40}O_8$: C, 69.54; H, 7.30. Found: C, 69.63; H, 7.30.

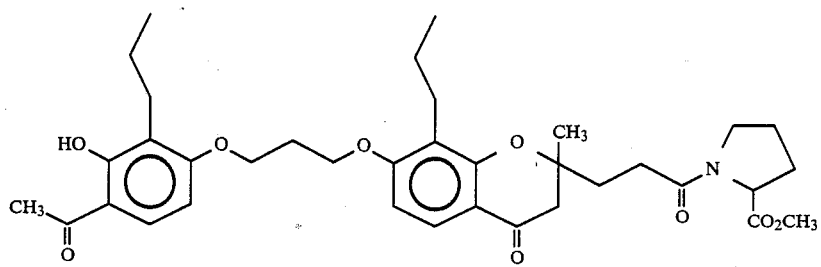

EXAMPLE 63

N-(3-[7-[3-(4-acetyl-3-hydroxy-2-propylphenoxy)-propoxy]-3,4-dihydro-2-methyl-4-oxo-8-propyl-2H-1-benzopyran-2-yl]propanoyl}-L-proline methyl ester that sodium hydroxide was used instead of lithium hydroxide. Structure assignment was supported by elemental analysis.

Analysis. Calcd. for $C_{35}H_{45}NO_9 \cdot H_2O$: C, 65.55; H, 7.38; N, 2.18. Found: C, 65.76; H, 7.44; N, 1.89.

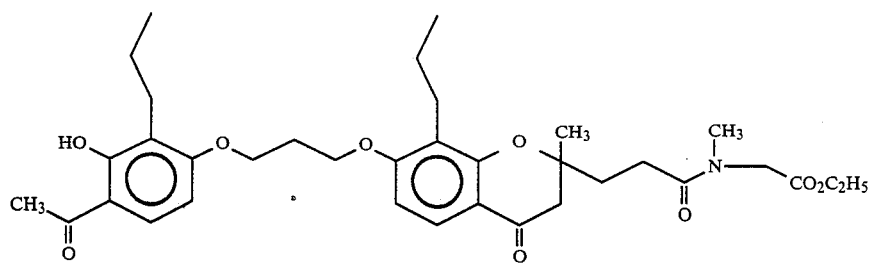

The title compound was prepareed by the methods of Examples 20 and 21 using L-proline methyl ester in place of dimethylamine. Structure assignment was confirmed by the nmr spectrum and by elemental analysis.

nmr (CDCl$_3$): δ(ppm) 1.35 (s, 3H, 2-methyl protons); 2.55 (s, 3H, acetyl CH$_3$); 3.71 (s, 3H, ester CH$_3$); 6.42, 6.55, 7.56, 7.72 (sets of d's, aromatic).

Analysis. Calcd. for $C_{36}H_{47}NO_9$: C, 67.80: H, 7.43; N, 2.20. Found: C, 67.68; H, 7.70; N, 2.15.

EXAMPLE 65

N-{3-[7-[3-(4-acetyl-3-hydroxy-2-propylphenoxy)-propoxy]-3,4-dihydro-2-methyl-4-oxo-8-propyl-2H-1-benzopyran-2-yl]propanoyl}sarcosine ethyl ester The title compound, m.p. 101°–102°, was prepared by the methods of Examples 20 and 21 using sarcosine ethyl ester in place of dimethylamine. Structure assignment was confirmed by the nmr spectrum and by ele-

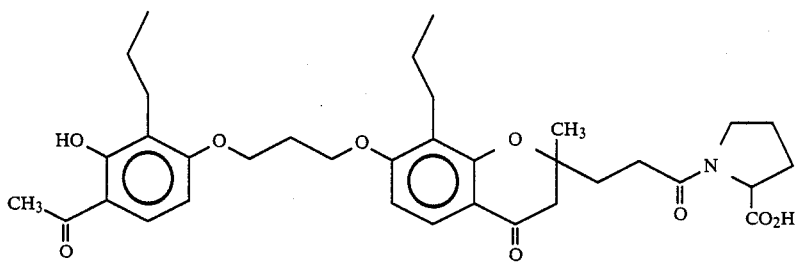

EXAMPLE 64

N-{3-[7-[3-(4-acetyl-3-hydroxy-2-propylphenoxy)-propoxy]-3,4-dihyro-2-methyl-4-oxo-8-propyl-2H-1-benzopyran-2-yl]propanoyl}-L-proline The title compound was prepared by the method of Example 7 using the title product of Example 63, except mental analysis.

nmr (CDCl$_3$): δ (ppm) 2.15 (s, 3H, N—CH$_3$); 2.55 (s, 3H, acetyl CH$_3$); 3.07 (s, 2H, N—ch$_2$—CO); 6.50 (overlapping d's, aromatic); 7.57, 7.72 (pair of d's, aromatic).

Analysis. Calcd. for $C_{34}H_{47}NO_9$: C, 67.18; H, 7.57; N, 2.24. Found: C, 67.12; H, 7.55; N, 2.19.

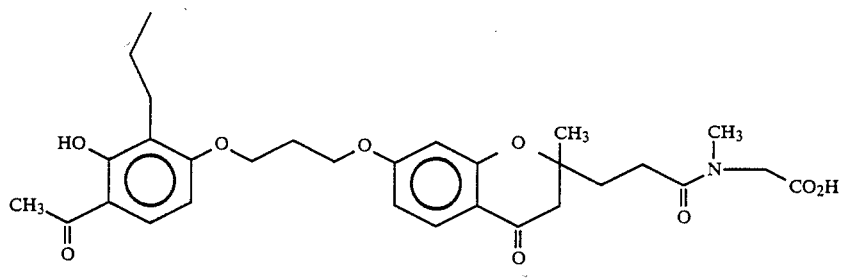

EXAMPLE 66

N-{3-[7-[3-(4-acetyl-3-hydroxy-2-propylphenoxy)-propoxy}-3,4-dihydro-2-methyl-4-oxo-8-propyl-2H-1-benzopyran-2-yl]propanoyl}sarcosine The title compound was prepared by the method of Example 7 using the title product of Example 65. Structure assignment was supported by elemental analysis.

Analysis. Calcd. for $C_{33}H_{43}NO_9 \cdot \frac{1}{2}H_2O$: C, 65.33; H, 7.31; N, 2.31. Found: C, 65.10; H, 7.40; N, 1.98.

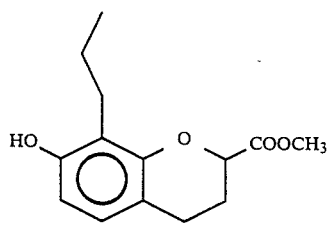

EXAMPLE 67 methyl 7-hydroxy-;b 3,4-dihydro-8-propyl-2H-1-benzopyran-2-oate

The title compound, m.p. 51°–53°, was prepared from the title product of Example 34 (6.6 g, 25 mmole) using the general method of Example 27, except that chromatographic eluent was 15% ethyl acetate-hexane. Structure assignment was supported by nmr, infrared, and ultraviolet spectra and by elemental analysis.

nmr (CDCl$_3$): δ (ppm) 0.95 (t, 3H, propyl CH$_3$); 3.77 (s, 3H, ester CH$_3$); 4.75 (t, 1H, 2-proton); 6.33, 6.72 (pair d's, aromatic).

IR (CHCl$_3$): 1740, 1760 cm$^{-1}$.

UV (methanol): $\lambda_{max}$ 284 nm ($\epsilon$ 1830).

Analysis. Calcd. for $C_{14}H_{18}O_4$: C, 67.18; H, 7.25. Found: C, 67.10; H, 7.42.

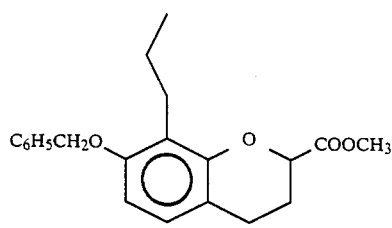

EXAMPLE 68 methyl 7-phenylmethoxy-3,4-dihydro-8-propyl-2H-1-benzopyran-2-oate

The title compound was prepared as an oil using the general method of Example 6 from the title product of Example 67 (5.25 g, 21 mmole) and benzyl bromide. Structure assignment was supported by nmr, infrared, and ultraviolet spectra and by elemental analysis.

nmr (CDCl$_3$): additional signals for benzyl protons at δ (ppm) 5.03, 7.38 (compare Example 67).

IR (CHCl$_3$): 1735, 1755 cm$^{-1}$.

UV (methanol): $\lambda_{max}$ 276 nm ($\epsilon$ 1862), 284 nm ($\epsilon$ 1933).

Analysis. Calcd. for $C_{21}H_{24}O_4$: C, 74.09; H, 7.11. Found: C, 74.11; H, 7.06.

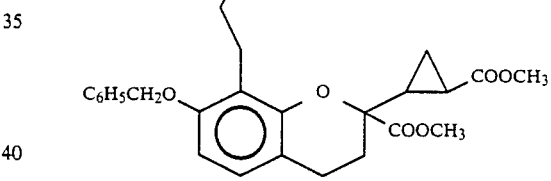

EXAMPLE 69 methyl 2-(7-phenylmethoxy-3,4-dihydro-2-methoxycarbonyl-8-propyl-2H-1-benzopyran-2-yl)1-cyclopropylcarboxylate To a solution under argon of 0.77 ml (ca. 5.5 mmole) of diisopropylamine in 300 ml of cold (−10°), dry tetrahydrofuran was added 2.1 ml of 2.5M n-butyl lithium in tetrahydrofuran. After the solution was cooled further to −70°, 1.7 g (5 mmole) of the title product of Example 68 in 10 ml of dry tetrahydrofuran was slowly added with stirring. After one hour a solution of 0.87 ml (ca. 6.3 mmole) of methyl 4-bromocrotonate in 10 ml of tetrahydrofuran was added slowly. The reaction mixture was allowed to warm to about 0;20 and then quenched with dilute hydrochloric acid. The mixture was poured into 150 ml of diethyl ether, washed sequentially with water, saturated sodium bicarbonate, and brine, and then dried over magnesium sulfate, filtered, and concentrated in vacuo to an oil. Purification by high performance liquid chromatography afforded the title compound as an oil which slowly crystallized, m.p. 82°–84°. Structure assignment was supported by nmr, infrared, and ultraviolet spectra and by elemental analysis.

nmr (CDCl$_3$): δ (ppm) 0.94 (t, 3H, propyl CH$_3$); 3.66, 3.68 (pair s's, 6H, ester CH$_3$'s); 5.02 (s, 2H, benzyl CH$_2$)-6.3–7.4 (aromatic)

IR (CHCl$_3$): 1720 cm$^{-1}$.

UV (methanol): λ$_{max}$ 276 nm (sh; ε 1875), 284 nm (ε 1964).

Analysis. Calcd. for C$_{26}$H$_{30}$O$_6$: C, 71.21; H, 6.90. Found: C, 70.41; H, 6.88.

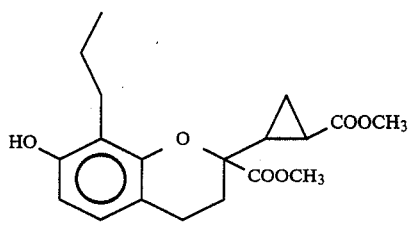

EXAMPLE 70 methyl 2-(7-hydroxy-3,4-dihydro-2-methoxycarbonyl-8-propyl-2H-1-benzopyran-2-yl)-1-cyclopropylcarboxylate The title compound (530 mg) was prepared from 699 mg (1.6 mmole) of the title product of Example 69 using the general method of Example 27, except that the hydrogenolysis solvent was ethanol. Structure assignment was supported by the nmr spectrum.

nmr (CDCl$_3$): loss of benzyl signals (compare Example 69).

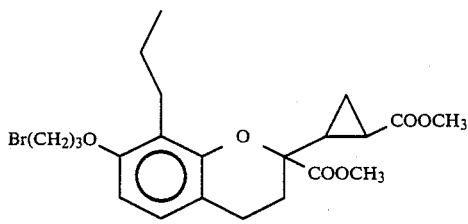

EXAMPLE 71 methyl 2-(7-(3-bromopropoxy-3,4-dihydro-2-methoxycarbonyl-8-propyl-2H-1-benzopyran-2-yl)-1-cyclopropylcarboxylate A mixture of 658 mg (1.7 mmole) of the title product of Example 70, 5.18 g (25.7 mmole) of 1,3-dibromopropane, 112 mg (0.75 mmole) of sodium iodide, and 480 mg (3.5 mmole) of anhydrous potassium carbonate was heated for three days at reflux in 15 ml of methyl ethyl ketone in the present of 3A molecular sieves. After removal of insolubles by filtration, the mixture was concentrated in vacuo to an oil. Purification by centrifugal thick-layer chromatography afforded 470 mg of the title compound as an oil, which was used in subsequent reactions without further purification.

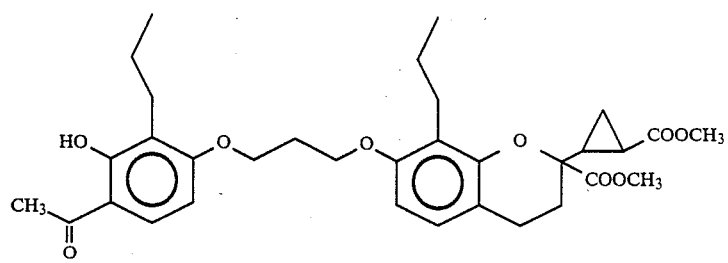

EXAMPLE 72 methyl 2-[7-[3-(4-acetyl-3-hydroxy-2-propylphenoxy)propoxy]-3,4-dihydro-2-methoxycarbonyl-8-propyl-2H-1-benzopyran-2-yl]-1-cyclopropylcarboxylate The title compound (209 mg) was prepared using the general method of Example 6 from the title product of Example 71 (470 mg, 0.90 mmole) and 2,4-dihydroxy-3-propylacetophenone. Structure assignment was supported by elemental analysis.

Analysis. Calcd. for C$_{33}$H$_{42}$O$_9$: C, 68.02; H, 7.26. Found: c, 67.44; H, 7.18.

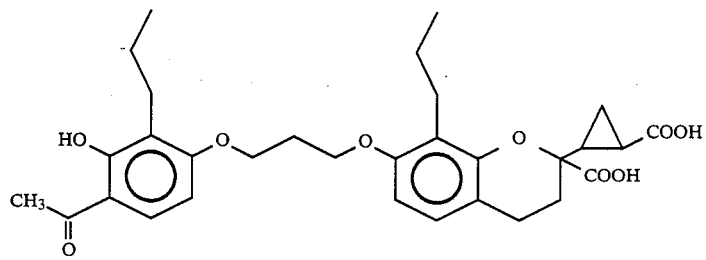

EXAMPLE 73

2-[7-[3-(4-acetyl-3-hydroxy-2-propylphenoxy)propoxy]-3,4-dihydro-2-carboxy-8-propyl-2H-1-benzopyran-2-yl]-1-cyclopropylcarboxylic acid The title compound, m.p. 138°–140°, was prepared from the title product of Example 72 using the method of Example 7, except that purification was effected by centrifugal thick-layer chromatography using 73:25:2 hexane-ethyl acetate-acetic acid as eluent. The resultant oil crystallized as the sesquihydrate upon standing.

Structure assignment was supported by the nmr spectrum and by elemental analysis.

nmr (CDCl$_3$): δ(ppm) 0.88, 0.90 (pair t's, 6H, propyl CH$_3$'s); 1.14 (m, 1H, cyclopropyl—CH distal to carbonyl); 2.00 (m, 1H, cyclopropyl—CH—COO—); 2.24 (t, 2H, cyclopropyl CH$_2$); 2.53 (s, 3H, acetyl CH$_3$); 6.3–7.3 (aromatic).

Analysis. Calcd. for C$_{31}$H$_{38}$O$_9$.3/2H$_2$O: C, 64.01; H, 7.11. Found: C, 64.26; H, 6.71.

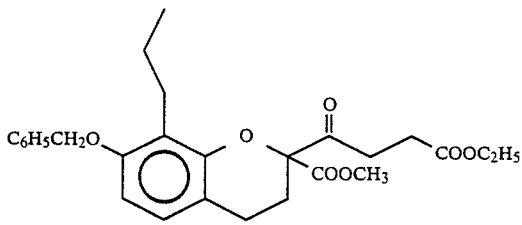

EXAMPLE 74 ethyl 4-(7-phenylmethoxy-3,4-dihydro-2-methoxy carbonyl-8-propyl-2H-1-benzopyran-2-yl]-4-oxobutanoate The title compound, (3.0 g) was prepared by the general method of Example 69 using N-(3-ethoxycarbonylpropanoyl)imidazole and, as before, the title compound of Example 68 (5.1 g, 15 mmole), except that the reaction was quenched with 0.5N sodium bisulfate and extracted using ethyl acetate before chromatography. Structure assignment was supported by nmr, infrared, and ultraviolet spectra and by elemental analysis.

nmr (CDCl$_3$): δ(ppm) 0.99 (t, 3H, propyl CH$_3$); 1.23, (t, 3H, ethyl CH$_3$); 3.71 (s, 3H, methyl ester CH$_3$ ); 4.10 (q, 2H, ethyl CH$_2$); 5.01 (s, 2H, benzyl CH$_2$); 6.3–7.4 (aromatic).

IR (CHCl$_3$): 1725, 1745 cm$^{-1}$.

UV (methanol) λ$_{max}$ 279 nm (sh; ε 2027), 284 nm (ε 2085)

Analysis. Calcd. for C$_{27}$H$_{32}$O$_7$: C, 69,21; H, 6.89. Found: C, 69.34; H, 6.94.

EXAMPLE 75 ethyl 4-[7-[3-(4-acetyl-3-hydroxy-2-propyl phenoxy)propoxy]-3,4-dihydro-2-methoxycarbonyl-8-propyl-2H-1-benzopyran-2-yl]-4-oxobutanoate The title compound (1.6 g) was prepared from the title product of Example 74 using the methods of Examples 70, 71 (but without chromatography), and 72 (except that 3 A molecular sieves were added to the reaction mixture). Purification was effected by high performance liquid chromatography using 20% ethyl acetate-hexane, followed by centrifugal thick-layer chromatography using 20% dioxane-hexane. Structure assignment was supported by nmr, infrared, and ultraviolet spectra and by elemental analysis.

nmr (CDCl$_3$): δ(ppm) 0.90, 0.95 (pair t, 6H, propyl CH$_3$'s); 1.23, (t, 3H, ethyl CH$_3$); 2.55 (s, acetyl CH$_3$); 3.69 (s, 3H, methyl ester CH$_3$); 6.3–7.4 (aromatic).

IR (CHCl$_3$): 1625, 1730, 1750 cm$^{-1}$.

UV (methanol): λ$_{max}$ 283 nm (ε 17690)

Analysis. Calcd. for C$_{34}$H$_{44}$O$_{10}$: C, 66.65; H, 7.24. Found: C, 66.62 H, 7.31.

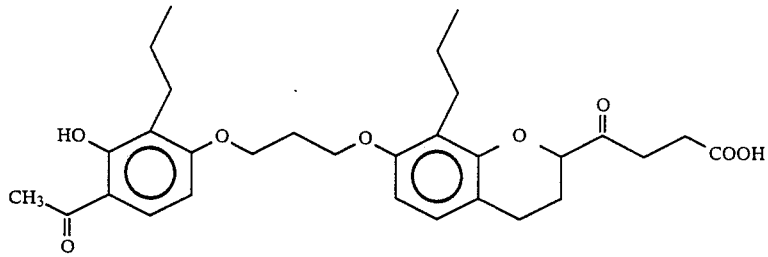

EXAMPLE 76

4-[7-[3-(4-acetyl-3-hydroxy-2-propylphenoxy) propoxy]-3,4-dihydro-8-propyl-2H-1-benzopyran-2-yl]-4-oxobutanoic acid The title compound, m.p. 100°–102°, was prepared from 1.1 g (1.8 mmole) of the title product of Example 75 using the method of Example 7, except that the reaction proceeded for four hours and sodium bisulfate was used to acidify the reaction mixture. The solid (700 mg) obtained by concentration of the ethyl acetate extracts to dryness was analytically pure. Structure assignment was supported by nmr, infrared, and ultraviolet spectra and by elemental analysis.

nmr (CHCl$_3$): loss of methyl and ethyl ester protons; addition of 2-proton at δ(ppm) 4.46 (dd, 1H) (compare Example 75).

IR (CHCl$_3$): 1630, 1715, 1750 cm$^{-1}$.

UV (methanol): λ$_{max}$ 284 nm (ε 18600).

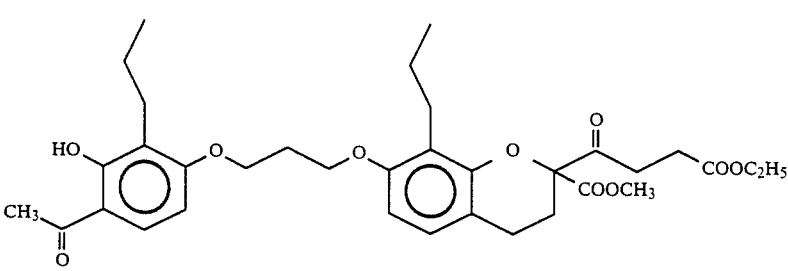

Analysis. Calcd. for $C_{30}H_{38}O_8$: C, 68.42; H, 7.27. Found: C, 68.12; H, 7.26.
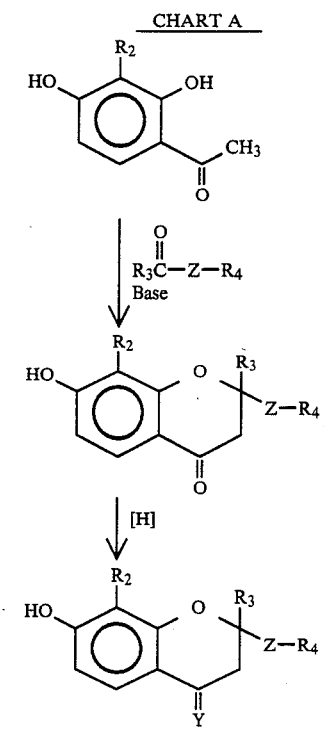
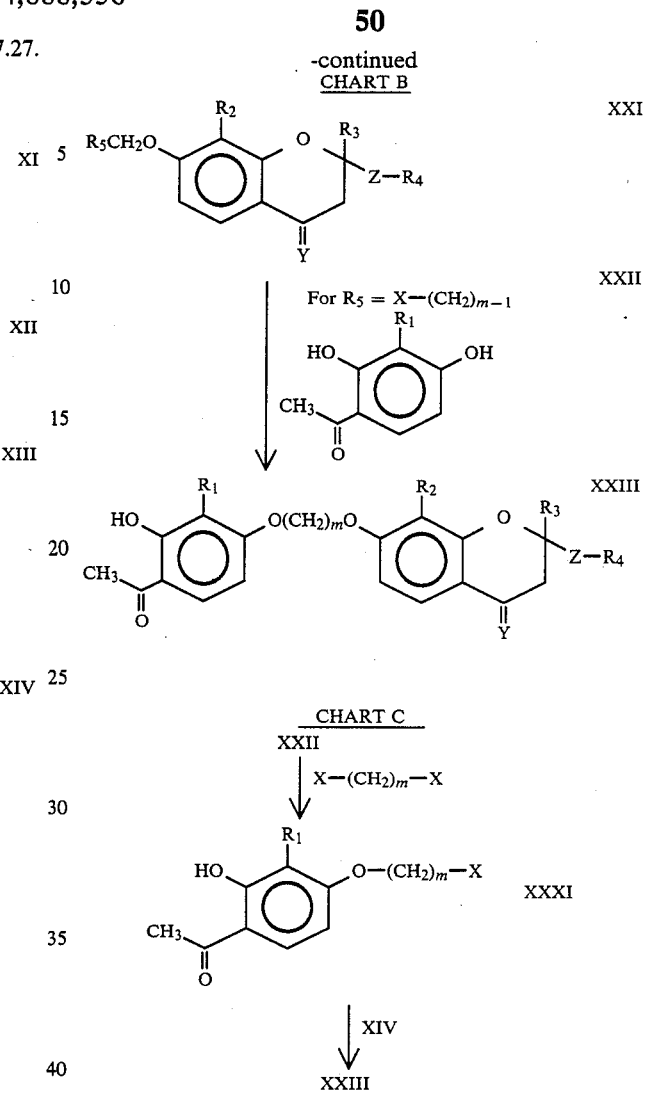
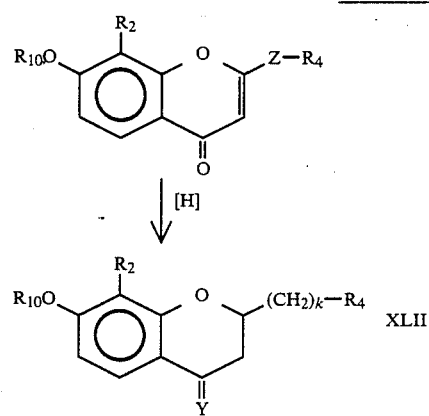
$Y = H, OH$
For $R_4 = \overset{O}{\underset{}{C}}$(alkyl)
$NaBH_4$

CHART D

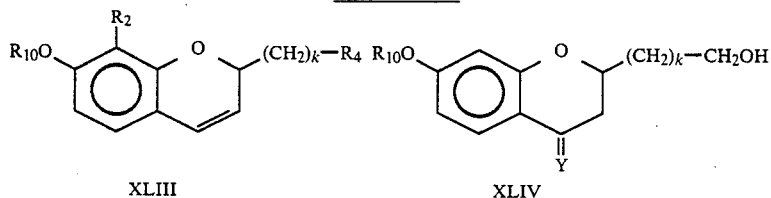

CHART E

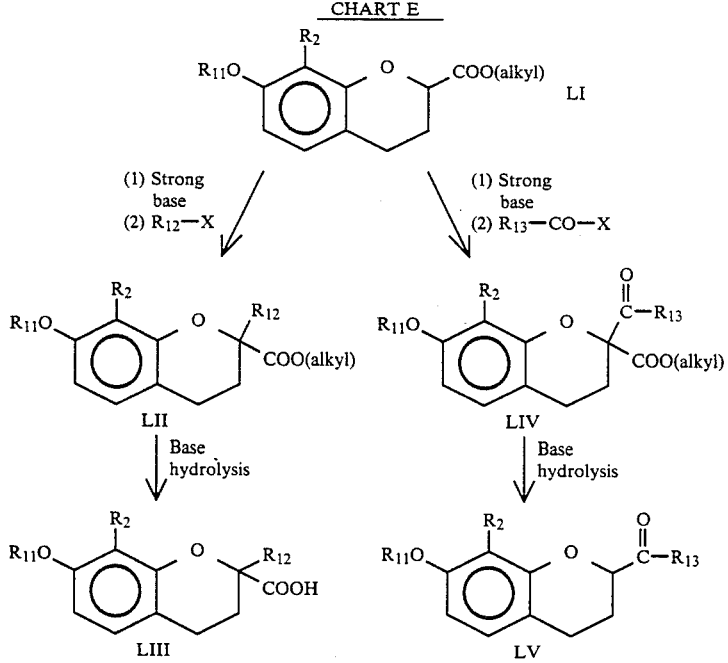

What is claimed is:

1. A pharmaceutical composition for the treatment of allergic reactions or inflammatory conditions associated with leukotriene $D_4$ comprising a compound of the formula

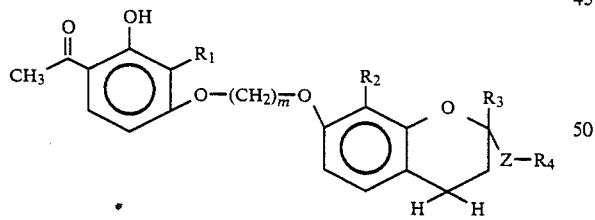

wherein Z is:
(a) $-(CH_2)_n-$; or
(b) $-(CH_2)_p-CH=CH-(CH_2)_q-$;
wherein m is an integer of from 2 to 6 inclusive;
wherein n is an integer of from 1 to 3 inclusive;
wherein p is an integer of from zero to 4 inclusive;
wherein q is an integer of from zero to 4 inclusive;
wherein p+q is equal to or less than 6;
wherein $R_1$, $R_2$ and $R_6$ are:
(a) alkyl of 1 to 6 carbon atoms, inclusive, each being the same or different;
wherein $R_3$ is
(a) hydrogen; or
(b) alkyl of 1 to 6 carbon atoms, inclusive;

wherein $R_4$ is:
(a) $-CO_2H$;
(b) $-CO_2R_6$;
(c) $-CONR_7R_8$; and
wherein $R_7$ and $R_8$ are:
(a) hydrogen;
(b) alkyl of 1 to 6 carbon atoms, inclusive $R_7$ and $R_8$ each being the same or different; or
(c) taken together with the nitrogen atom to which they are attached form a 5 or 6 member saturated N-heterocycle optionally substituted by carboxylic acid or methyl ester thereof with the balance of the members being carbon;
or the pharmacologically acceptable addition salts thereof; and a pharmaceutically acceptable carrier.

2. A pharmaceutical composition according to claim 1 wherein $R_3$ is alkyl.

3. A pharmaceutical composition according to claim 2 wherein said compound is methyl 3-[7-[3-(4-acetyl-3-hydroxy-2-propylphenoxy)-propoxyl]-3,4-dihydro-2-methyl-8-propyl-2H-1-benzopyran-2-yl]propanoate.

4. A pharmaceutical composition according to claim 2 wherein said compound is 3-[7-[3-(4-acetyl-3-hydroxy-2-propylphenoxy)propoxy]-3,4-dihydro-2-methyl-8-propyl-2H-1-benzopyran-2-yl]propanoic acid.

5. A pharmaceutical composition according to claim 1 wherein $R_3$ is —H.

6. A pharmaceutical composition according to claim 5 wherein said compound is ethyl 3-[7-[3-(4-acetyl-3- hydroxy-2-propylphenoxy]-3,4-dihydro-8-propyl-2H-1-benzopyran-2-yl]propanoate.

7. A pharmaceutical composition according to claim 5 wherein said compound is 3-[7-[3-(4-acetyl-3-hydroxy-2-propylphenoxy)propoxy]-3,4-dihydro-8-propyl-2H-1-benzopyran-2-yl]propanoic acid.

8. A pharmaceutical composition for the treatment of allergic reactions or inflammatory conditions associated with leukotriene $D_4$ comprising a compound of the formula

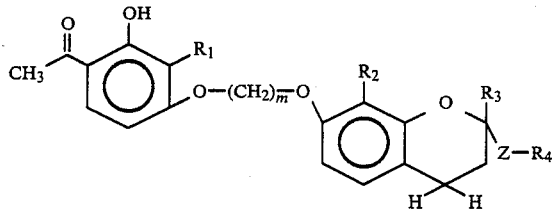

wherein Z is:
(a) $-(CH_2)_n-$; or
(b) $-(CH_2)_p-CH=CH-(CH_2)_q-$;
wherein m is an integer of from 2 to 6 inclusive;
wherein n is an integer of from 1 to 3 inclusive;
wherein p is an integer of from zero to 4 inclusive;
wherein q is an integer of from zero to 4 inclusive;
wherein p+q is equal to or less than 6;
wherein $R_1$, $R_2$ and $R_6$ are:
(a) alkyl of 1 to 6 carbon atoms, inclusive, each being the same or different;
wherein $R_3$ is
(a) hydrogen; or
(b) alkyl of 1 to 6 carbon atoms, inclusive;
wherein $R_4$ is:
(a) $-CO_2H$;
(b) $-CO_2R_6$;
(c) $-CONR_7R_8$; and
wherein $R_7$ and $R_8$ are:
(a) hydrogen;
(b) alkyl of 1 to 6 carbon atoms, inclusive, $R_7$ and $R_8$ each being the same or different; or the pharmacologically acceptable addition salts thereof; and a pharmaceutically acceptable carrier.

9. A method of treating allergic reactions associated with leukotriene $D_4$ in a mammal comprising administering a therapeutically effective amount of the pharmaceutical composition of claim 1 to a mammal in need of such treatment.

10. A method of treating allergic reactions associated with leukotriene $D_4$ in a mammal comprising administering a therapeutically effective amount of the pharmaceutical composition of claim 2 to a mammal in need of such treatment.

11. A method of treating allergic reactions associated with leukotriene $D_4$ in a mammal comprising administering a therapeutically effective amount of the pharmaceutical composition of claim 3 to a mammal in need of such treatment.

12. A method of treating allergic reactions associated with leukotriene $D_4$ in a mammal comprising administering a therapeutically effective amount of the pharmaceutical composition of claim 4 to a mammal in need of such treatment.

13. A method of treating allergic reactions associated with leukotriene $D_4$ in a mammal comprising administering a therapeutically effective amount of the pharmaceutical composition of claim 5 to a mammal in need of such treatment.

14. A method of treating allergic reactions associated with leukotriene $D_4$ in a mammal comprising administering a therapeutically effective amount of the pharmaceutical composition of claim 6 to a mammal in need of such treatment.

15. A method of treating allergic reactions associated with leukotriene $D_4$ in a mammal comprising administering a therapeutically effective amount of the pharmaceutical composition of claim 7 to a mammal in need of such treatment.

16. A method of treating allergic reactions associated with leukotriene $D_4$ in a mammal comprising administering a therapeutically effective amount of the pharmaceutical composition of claim 8 to a mammal in need of such treatment.

17. A method of treating inflammatory conditions associated with leukotriene $D_4$ in a mammal comprising administering a therapeutically effective amount of the pharmaceutical composition of claim 1 to a mammal in need of such treatment.

18. A method of treating inflammatory conditions associated with leukotriene $D_4$ in a mammal comprising administering a therapeutically effective amount of the pharmaceutical composition of claim 2 to a mammal in need of such treatment.

19. A method of treating inflammatory conditions associated with leukotriene $D_4$ in a mammal comprising administering a therapeutically effective amount of the pharmaceutical composition of claim 3 to a mammal in need of such treatment.

20. A method of treating inflammatory conditions associated with leukotriene $D_4$ in a mammal comprising administering a therapeutically effective amount of the pharmaceutical composition of claim 4 to a mammal in need of such treatment.

21. A method of treating inflammatory conditions associated with leukotriene $D_4$ in a mammal comprising administering a therapeutically effective amount of the pharmaceutical composition of claim 5 to a mammal in need of such treatment.

22. A method of treating inflammatory conditions associated with leukotriene $D_4$ in a mammal comprising administering a therapeutically effective amount of the pharmaceutical composition of claim 6 to a mammal in need of such treatment.

23. A method of treating inflammatory conditions associated with leukotriene $D_4$ in a mammal comprising administering a therapeutically effective amount of the pharmaceutical composition of claim 7 to a mammal in need of such treatment.

24. A method of treating inflammatory conditions associated with leukotriene $D_4$ in a mammal comprising administering a therapeutically effective amount of the pharmaceutical composition of claim 8 to a mammal in need of such treatment.

* * * * *

UNITED STATES PATENT AND TRADEMARK OFFICE
CERTIFICATE OF CORRECTION

PATENT NO. : 4,888,356

DATED : December 19, 1989

INVENTOR(S) : Miyano, et al.

It is certified that error appears in the above-identified patent and that said Letters Patent is hereby corrected as shown below:

Column 1, lines 6-7, reading "Ser. No. 0/681,038 filed Dec. 12, 1984, 1 now" should read -- Ser. No 06 /681,038 filed Dec. 12, 1984, now --.
Column 1, line 17, reading "Ser. No. 0/520,973" should read -- Ser. No. 06/520, 973--.
Column 1, the first structure, that portion of the structure reading

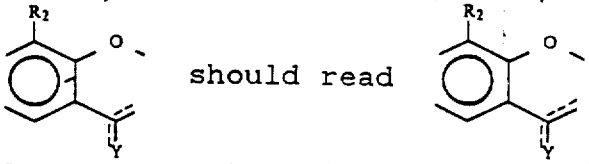 should read 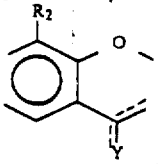

Column 2, line 39, reading "alkyl or" should read -- alkyl of --.
Column 10, line 1, reading "EXAMPLE 20" should read -- EXAMPLE 10 --.
Column 16, line 31, reading "3.09" should read -- 3.06 --.
Column 20, line 42, reading "(m, b 1H," should read -- (m, 1H, --.
Column 23, line 64, reading "nMr" should read -- nmr --.
Column 28, the first structure, that portion of the structure reading

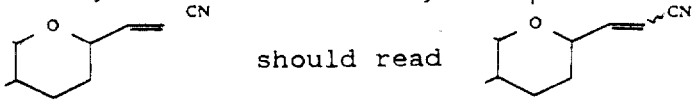 should read 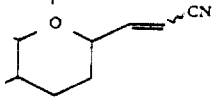

Column 28, lines 37-38, reading "-8-propyl2H-1-benzopyran-2yl]" should read -- -8-propyl-2H-1-benzopyran-2-yl] --.
Column 31, line 62, reading "-propyl2H-" should read -- -propyl-2H- --.
Column 32, lines 35-36, reading "-2propylphenoxy)propoxy]-8-propyl-2H -1benzopyran-" should read -- -2-propylphenoxy)propoxy]-8-propyl-2H-1-benzopyran- --.
Column 32, line 37, reading "As solution" should read -- A solution --.
Column 33, line 16, reading "-benzopyran2-" should read -- -benzopyran-2- --.
Column 35, line 5, reading "-7hydroxy-2-methyl8propyl-" should read -- -7-hydroxy-2-methyl-8-propyl- --.
Column 35, the first structure, that portion of the structure reading

UNITED STATES PATENT AND TRADEMARK OFFICE
CERTIFICATE OF CORRECTION

PATENT NO. : 4,888,356
DATED : December 19, 1989
INVENTOR(S) : Miyano, et al.

It is certified that error appears in the above-identified patent and that said Letters Patent is hereby corrected as shown below:

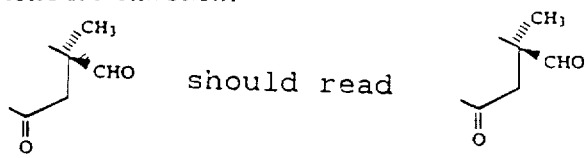

Column 38, line 1, reading "$C_{18}H_{22};1\ O_5$" should read -- $C_{18}H_{22}O_5$ --.

Column 41, lines 17-19, reading "N-(3-" should read -- N-{3- --.
Column 42, line 65, reading "-ch$_2$-" should read -- -CH$_2$- --.
Column 43, line 21, reading "propoxy}-3" should read -- propoxy]-3 --.
Column 43, line 42, reading "7-hydroxy-;b" should read -- 7-hydroxy- --.
Column 44, line 58, reading "0;20" should read -- 0° --.
Column 52, line 59, reading "-propoxyl]-" should read -- -propoxy]- --.

Signed and Sealed this

Twelfth Day of May, 1992

Attest:

DOUGLAS B. COMER

Attesting Officer    Acting Commissioner of Patents and Trademarks